(12) United States Patent
Dobson et al.

(10) Patent No.: US 10,137,149 B2
(45) Date of Patent: Nov. 27, 2018

(54) PARTICLES FOR THE TREATMENT OF CANCER IN COMBINATION WITH RADIOTHERAPY

(75) Inventors: Peter James Dobson, Oxford (GB); Gareth Wakefield, Oxford (GB); Helen Elizabeth Townley, Oxford (GB)

(73) Assignee: Oxford University Innovation Limited (GB)

( * ) Notice: Subject to any disclaimer, the term of this patent is extended or adjusted under 35 U.S.C. 154(b) by 0 days.

(21) Appl. No.: 13/514,487

(22) PCT Filed: Dec. 8, 2010

(86) PCT No.: PCT/GB2010/002247
§ 371 (c)(1),
(2), (4) Date: Jul. 24, 2012

(87) PCT Pub. No.: WO2011/070324
PCT Pub. Date: Jun. 16, 2011

(65) Prior Publication Data
US 2012/0282185 A1    Nov. 8, 2012

(30) Foreign Application Priority Data
Dec. 9, 2009    (GB) .................................. 0921596.3

(51) Int. Cl.
| | | |
|---|---|---|
| A61K 49/04 | (2006.01) | |
| A61K 33/24 | (2006.01) | |
| A61K 41/00 | (2006.01) | |
| A61K 45/06 | (2006.01) | |
| B82Y 5/00 | (2011.01) | |

(52) U.S. Cl.
CPC .......... *A61K 33/24* (2013.01); *A61K 41/0038* (2013.01); *A61K 45/06* (2013.01); *B82Y 5/00* (2013.01)

(58) Field of Classification Search
CPC ...... A61K 33/00; A61K 33/24; A61K 49/002; A61K 49/04; A61K 49/0414; A61N 5/10; C07F 11/005
See application file for complete search history.

(56) References Cited

U.S. PATENT DOCUMENTS

| | | | |
|---|---|---|---|
| 6,689,338 | B2 | 2/2004 | Kotov |
| 6,869,596 | B1 | 3/2005 | Knowland et al. |
| 7,132,122 | B2 | 11/2006 | Parikh et al. |
| 7,169,196 | B2 | 1/2007 | Wakefield |
| 7,267,875 | B2 | 9/2007 | Whiteford et al. |
| 2003/0138386 | A1 | 7/2003 | Knowland et al. |
| 2004/0254419 | A1 | 12/2004 | Wang et al. |
| 2006/0210798 | A1 | 9/2006 | Burda |
| 2006/0281087 | A1 | 12/2006 | Sonezaki et al. |
| 2007/0190765 | A1 | 8/2007 | Xie et al. |
| 2007/0202334 | A1 | 8/2007 | Xie et al. |
| 2007/0217996 | A1 | 9/2007 | Levy et al. |
| 2007/0274909 | A1 | 11/2007 | Justel et al. |
| 2007/0292353 | A1 | 12/2007 | Levy et al. |
| 2008/0138296 | A1 | 6/2008 | Tamarkin et al. |
| 2008/0176076 | A1* | 7/2008 | Van Veggel et al. ......... 428/404 |
| 2009/0005238 | A1 | 1/2009 | Falaras |
| 2009/0028792 | A1 | 1/2009 | Schwartz et al. |
| 2009/0110929 | A1* | 4/2009 | Li et al. ........................ 428/402 |
| 2009/0155173 | A1 | 6/2009 | Scherman et al. |
| 2009/0202650 | A1* | 8/2009 | Hwu et al. .................... 424/491 |
| 2009/0220561 | A1 | 9/2009 | Jin et al. |
| 2010/0178512 | A1 | 7/2010 | Giesenberg et al. |
| 2010/0303722 | A1 | 12/2010 | Jin et al. |

FOREIGN PATENT DOCUMENTS

| | | |
|---|---|---|
| CN | 101116808 A1 | 2/2008 |
| EP | 1920784 A1 | 5/2008 |
| JP | 2008184357 A1 | 8/2008 |
| WO | 9502324 A1 | 1/1995 |

OTHER PUBLICATIONS

Rozhkova EA, et al. 2009. A High-Performance Nanobio Photocatalyst for Targeted Brain Cancer Therapy. Nanoletters; 9(9): 3337-3342.*
Liss et al. Textures and Microstructures. 2003; 35: 219-252.*
Xu, Huang, Xiao, and Lu, "Photoexcited TiO2 nanoparticles through OH-radicals induced malignant cells to necrosis", Supramolecular Science, vol. 5, 1998, pp. 449-451.
Ishibashi, Fujishima, Watanabe, and Hashimoto, "Detection of active oxidative species in TiO2 photocatalysis using the fluorescence technique", Electrochemistry Comm., vol. 2, 2000, pp. 207-210.
Tkachenko, Xie, Coleman, Glomm, Ryan, Anderson, Franzen, and Feldheim, "Multifunctional Gold Nanoparticle-Peptide Complexes for Nuclear Targeting", J. Am. Chem. Soc., vol. 124, 2003, pp. 4700-4701.
Townley, Rapa, Bumb, Morten, and Dobson, "Novel nanoparticles for imaging, diagnostics, and therapy in cancer patients: Find, Fight, Follow," Poster Presentation at NanoEurope 2008 (St. Gallen, Switzerland).
Melancon, Lu, and Li, "Gold-based Magneto/Optical Nanostructures: Challenges for in Vivo Applications in Cancer Diagnostics and Therapy", MRS Bulletin, vol. 34, 2009, pp. 415-421.
El-Bahy, Ismail, and Mohamed, "Enhancement of titania by doping rare earth for photodegradation of organic dye (Direct Blue)", Journal of Hazardous Materials, vol. 166, 2009, pp. 138-143.

(Continued)

*Primary Examiner* — David Browe
(74) *Attorney, Agent, or Firm* — Luedeka Neely Group, PC

(57) ABSTRACT

The invention provides a particle comprising a metal oxide which is doped with at least one rare earth element, wherein the metal oxide is selected from titanium dioxide, zinc oxide, cerium oxide and mixtures of two or more thereof. The invention also provides a pharmaceutical composition comprising the particles, and to uses of the particles and composition in the treatment and diagnosis of cancer.

17 Claims, 8 Drawing Sheets

(56) References Cited

OTHER PUBLICATIONS

Paunesku, Ke, Dharmakumar, Mascheri, Wu, Lai, Vogt, Maser, Thurn, Szolc-Kowalska, Larson, Bergan, Omary, Li, Lu, and Woloschak, "Gadolinium-conjugated TiO2-DNA oligonucleotide nanoconjugates show prolonged intracellular retention period and T1-weighted contrast enhancement in magnetic resonance images", Nanomedicine: Nanotechnoloby, Biology, and Medicine, vol. 4, 2008, pp. 201-207.

Zhou, Zhou, and Tang, "Formation of TiO2 nano-fiber doped with Gd3+ and its photocatalytic activity", Materials Letters, vol. 59, 2005, pp. 3115-3118.

Wang, Mao, Zhang, and Tu, "Nano-cerium-element-doped titanium dioxide induces apoptosis of Bel 7402 human hepatoma cells in the presence of visible light", World J. Gastroenterol., vol. 13, Aug. 7, 2007, pp. 4011-4014.

Lazau, Mocanu, Miron, Sfirloaga, Tanasie, Tatu, Gruia, and Grozescu, "Consideration regarding the use of TiO2 doped nanoparticles in medicine", Digest Journal of Nanomaterials and Biostructures, vol. 2, No. 3, 2007, pp. 257-263.

Taoda, Hiroshi, "Material Development, industrial Application and International Standardizatio of Photocatalyst," J. Vac. Soc. Jpn. vol. 49, No. 4, (2006), pp. 238-242.

Tamura, Kazuhisa; Ooko, Yoshihisa, The Activation of Photocatalysts upon X-ray irradiation, Engineering Materials vol. 55, Issue 12, (2007), pp. 80-84.

Xu, An-Wu; Gao, Yuan; Liu, Han-Qin, "The Preparation, Characterizaation, and Their Photocatalytic Activities of Rare-Earch-Doped TiO2 Nanoparticles," Journal of Catalysis, vol. 207, 2002, pp. 151-157.

Yang, Ping; Lu, Cheng; Hua, Nanping, Du, Yukou,"Titanium dioxide nanoparticles co-doped with Fe3+ and Eu3+ ions for photocatalysis," Materials Letters 57 (2002), pp. 794-801.

Kato, Risa; Shimura, Naoki; Ogawa, Makoto,"Controlled Photocatalytic Ability of Titanium Dioxide Particle by Coating with Nanoporous Silica," Chemistry Letters vol. 37, No. 1 (2008), pp. 76-77.

"Engineering Materials" vol. 55, Issue 12, (2007), pp. 80-84.

Tamura, Kazuhisa; Ohko, Yoshihisa; Kawamura, Hiroyuki; Yoshikawa, Hideki; Tatsuma, Tetsu; Fujishima, Akira; Mizuki, Jun'Ichiro, "X-Ray Induced Photoeletrochemistry on TiO2," Electrochimica Acta, vol. 52 (2007), pp. 6938-6942.

Rozhkova, Elena A.; Ulasov, Llya; Lai, Barry; Dimitrijevic, Nada M.; Lesniak, Maciej S.; Rajh, Tijana, "A High-Performance Nanobio Photocatalyst for Targeted Brain Cancer Therapy," Nano Letters, vol. 9, No. 9 (2009), pp. 3337-3342.

Kubota, Y.; Shuin, T.; Kawasaki, C.; Hosaka, M.; Kitamura, H.; Cai, R.; Sakai, H.; Hashimoto, K.; Fujishima, A., "Photokilling of T-24 human bladder cancer cells with titanium dioxide," Br. J. Cancer vol. 70, (1994), pp. 1107-1111.

Cai, Ruxiong; Kubota, Yoshinobu; Shuin, Taro; Sakai, Hideki; Hashimoto, Kazuhito; Fujishima, Akira, "Induction of Cytotoxicity by Photoexcieted TiO2 Particles," Cancer Research vol. 52, Apr. 15, 1992, pp. 2346-2348.

* cited by examiner

PARTICLES FOR THE TREATMENT OF CANCER IN COMBINATION WITH RADIOTHERAPY

FIELD OF THE INVENTION

The invention relates to a particle comprising a doped metal oxide, which generates free radicals on excitation by X-rays, such as from X-rays that are used as part of a radiotherapy treatment. The invention further relates to compositions comprising the particle, and to uses of the particle and the compositions in the treatment and diagnosis of cancer.

BACKGROUND TO THE INVENTION

Photodynamic therapy (PDT) is commonly used to treat some types of cancer. PDT involves injecting a photosensitizing agent into the bloodstream of a patient. The agent is absorbed by cells all over the body, but it generally accumulates in the tumour due to abnormalities or defects in the tumour vasculature. It is also rapidly absorbed by cancer cells, which tend to grow and divide much more quickly than healthy cells and hence have a higher metabolic activity.

Approximately 24 to 72 hours after the injection, when most of the agent has left the normal cells but remains in the tumour, only the tumour is exposed to light of a specific frequency, such as UV light or laser light. The photosensitizing agent that has accumulated in the tumour is excited by exposure to this light and reacts with nearby oxygen or water molecules in the tissue to produce reactive oxygen species (ROS), such as singlet oxygen (average lifetime of 3.7 ms and a diffusion distance of 82 nm), a superoxide radical (average lifetime of 50 ms and a diffusion distance of 320 nm) or a hydroxyl radical (average lifetime of $10^{-7}$ s and a diffusion distance of 4.5 nm). The ROS produced overwhelm the antioxidant defence capacity of nearby cells thereby resulting in the destruction of cancer cells in the tumour.

The short life-times and diffusion distances of the ROS allow cancer cells to be destroyed with little or no damage being caused to neighbouring healthy cells. In addition to directly killing cancer cells, PDT also appears to shrink or destroy tumours by damaging blood vessels in the tumour, thereby depriving it of nutrients. A further benefit is that PDT may also activate the immune system of the patient to attack the tumour cells.

Titanium dioxide is known to generate ROS on exposure to UV light. In fact, the effect of titanium dioxide on cultured human adenocarcinoma cells after UV irradiation has been investigated (Xu et al., Supramolecular Science, 5 (1998), 449-451). In this study, transmission electron microscopy (TEM) showed disruption to the cellular membrane and endomembrane system of the cells as a result of oxidative stress. It is believed that the titanium dioxide particles produce hydroxyl radicals that oxidize the membrane lipids of the cells to produce peroxidants, which then set up a series of peroxidant chain reactions. The oxidatively stressed malignant cells progress to a necrotic state that results in their destruction.

Titanium dioxide and many of the photosensitizing agents used in PDT are excited by light of a specific wavelength that cannot penetrate deep into a human body. Consequently, PDT has been limited to the treatment of superficial cancers, such as skin cancers.

Cancers in other locations of the body may instead be treated using radiotherapy, which involves the use of ionizing radiation, such as X-rays. However, some types of cancer, such as renal cell cancer, are radioresistant because the doses of radiation required to destroy the cancer are too high to be safe in clinical practice. Higher doses of radiation are also associated with an increased risk of causing cancer. There is therefore a need for an agent that will enhance or improve existing radiotherapy treatments.

International patent application no. PCT/FR2005/001145 (WO 2005/120590) describes composite or aggregate particles that are activatable by X-rays. The particles are composed of two distinct inorganic compounds, which are arranged to be near to one another. The first inorganic compound is able to absorb X-rays and then emit UV-visible light. The second inorganic compound can absorb UV-visible light and then generate free radicals on contact with water or oxygen. Such an arrangement of compounds allows X-rays to be used to generate ROS by a stepwise excitation process. However, there are energy losses associated with each excitation step, such that the amount of ROS generated per unit dose of X-rays is relatively low.

SUMMARY OF THE INVENTION

The inventors have found that, by doping titanium dioxide, zinc oxide or cerium oxide with a rare earth element, the resulting doped metal oxide can itself be directly excited by X-rays to generate free radicals, particularly reactive oxygen species (ROS), in large amounts per unit dose of X-rays. Treatment of cancer by X-ray excitation of particles localised at a cancer site is a minimally invasive procedure and would be able to utilise existing clinical facilities.

ROS can react with biological molecules, modify the structure and function of proteins and cause oxidative damage to cellular DNA by destroying bases and producing single strand breaks. In addition, oxidants are known to act on mitochondria to trigger the initiation of apoptosis. Consequently, the generation and control of ROS at a tumour site can be used to kill malignant cells.

Accordingly, the invention provides a particle comprising a metal oxide which is doped with at least one rare earth element, wherein the metal oxide is selected from titanium dioxide, zinc oxide, cerium oxide and mixtures of two or more thereof. In one preferred aspect, the invention relates to a particle comprising a metal oxide doped with at least two different rare earth elements selected from La, Ce, Pr, Nd, Sm, Eu, Gd, Tb, Dy, Ho, Er, Tm, Yb and Lu, wherein the metal oxide is titanium dioxide.

In general, the invention is concerned with a plurality of such particles, uses and methods thereof.

Composite particles having a core-shell structure or particles that are composed of an aggregate of nanoparticles are difficult to produce at sizes suitable for effectively treating cancer. Such particles are not as efficient at generating ROS due to vacancies, impurities and defects that may be present in each of the component materials. The invention provides a particle made of a single active material (e.g. the doped metal oxide) that generates ROS upon direct exposure only to X-rays. The active material, such as that present in a single phase particle, can be tuned by the selection of one or more appropriate rare earth element dopants to be excited by a specific X-ray source. Particles composed of the material can readily be produced in a size that is effective for the treatment of cancer.

In the invention, ROS are generated directly from X-ray irradiation of the titanium dioxide, zinc oxide or cerium oxide that is doped with at least one rare earth element. The presence of an additional inorganic compound that emits UV-visible light on exposure to X-rays is not essential for the generation of ROS.

Typically, a particle of the invention does not comprise or include a further inorganic compound that absorbs X-rays and emits UV-visible light, such as one or more of $Y_2O_3$, $(Y, Gd)_2O_3$, $CaWO_4$, $GdO_2S$, $LaOBr$, $YTaO_3$, $BaFCl$, $Gd_2O_2S$, $Gd_3Ga_5O_{12}$, $Rb_3Lu(PO_4)_2$, $HfGeO_4$ and $Cs_3Lu(PO_4)_2$, each of which may optionally be doped with a rare earth element.

Generally, the invention provides a particle consisting essentially of (i) a metal oxide which is doped with at least one rare earth element, wherein the metal oxide is selected from titanium dioxide, zinc oxide, cerium oxide and mixtures of two or more thereof; and optionally (ii) one or more of a coating, a linker group, a targeting moiety, an optical contrast agent, a radioisotope, a paramagnetic contrast agent or a superparamagnetic contrast agent.

It is preferred that a particle of the invention is not a composite particle or an aggregate of nanoparticles, particularly a composite particle or nanoparticle aggregate that includes one or more of $Y_2O_3$, $(Y, Gd)_2O_3$, $CaWO_4$, $GdO_2S$, $LaOBr$, $YTaO_3$, $BaFCl$, $Gd_2O_2S$, $Gd_3Ga_5O_{12}$, $Rb_3Lu(PO_4)_2$, $HfGeO_4$ and $Cs_3Lu(PO_4)_2$, each of which may optionally be doped with a rare earth element, or generally an inorganic compound that absorbs X-rays and emits UV-visible light.

In another aspect of the invention, the particle of the invention is for use in the treatment of the human or animal body by therapy, preferably when used in combination with X-ray radiation. Typically, the therapy is X-ray radiotherapy. The invention provides a particle for use in the treatment of cancer. In a preferred aspect, the invention relates to a particle for use in combination with X-ray radiation in the treatment of cancer, wherein the particle comprises a metal oxide, which metal oxide is titanium dioxide and is doped with at least one rare earth element. Preferably, the particle comprises a core consisting of the metal oxide.

The invention further relates to the use of the particle for the manufacture of a medicament for the treatment of cancer when used in combination with X-ray radiation (e.g. when used in combination with X-ray radiotherapy).

The invention also provides pharmaceutical composition comprising (i) a plurality of the particles of the invention and optionally (ii) one or more pharmaceutically acceptable ingredients. In a further aspect of the invention, the pharmaceutical composition is for use in the treatment of the human or animal body by therapy, preferably when used in combination with X-ray radiation. Typically, the therapy is X-ray radiotherapy. The invention provides a pharmaceutical composition for use in the treatment of cancer.

The invention also relates to the use of the pharmaceutical composition for the manufacture of a medicament for the treatment of cancer in combination with X-ray radiation (e.g. when used in combination with X-ray radiotherapy).

Another aspect of the invention is a combination comprising (a) a plurality of the particles of the invention and (b) a radiosensitizing agent.

The invention further provides a product comprising (a) a plurality of particles of the invention and (b) a radiosensitizing agent, as a combined preparation for simultaneous, concurrent, separate or sequential use in the treatment of cancer when used in combination with X-ray radiation.

A further aspect of the invention relates to a method for treating cancer comprising administering to a subject a particle or a pharmaceutical composition of the invention, and directing X-ray radiation to a locus or site of the cancer or tumour tissue.

The invention also provides an in vitro method of destroying cancer cells comprising adding a particle or a pharmaceutical composition as described herein to a cell culture, medium or solution comprising cancer cells, then directing X-ray radiation at the cancer cells.

As explained above, the particles of the invention accumulate in the tissue of a tumour or in cancer cells. Due to the presence of the heavy rare earth element, the presence of the particles of the invention localised in a tumour or cancer cells may be imaged using X-rays. This may allow diagnosis of the presence of a tumour or of cancer cells in a patient, and allow the treatment of the tumour or cancel cells to be monitored.

A further aspect of the invention, relates to a particle or pharmaceutical composition of the invention for use in a diagnostic method practised on the human or animal body. The invention further relates to the use of a particle or a pharmaceutical composition of the invention for diagnosing the presence or absence of cancer.

The invention further provides a method for diagnosing the presence or absence of cancer comprising administering to a subject a particle or a pharmaceutical composition of the invention, then detecting the presence or absence of the particle or the pharmaceutical composition at a locus or site suspected of being cancerous.

The invention also provides a method of preparing a particle of the invention, which method comprises the step of heating a particle at a temperature of 400° C. or more, wherein the particle comprises a metal oxide which is doped with at least one rare earth element, wherein the metal oxide is selected from titanium dioxide, zinc oxide, cerium oxide and mixtures of two or more thereof. In a preferred aspect, the metal oxide is titanium dioxide.

DETAILED DESCRIPTION OF THE INVENTION

Limitations associated with the use of UV light can be overcome by using a more penetrating energy source such as X-rays to trigger a photocatalytic reaction, such as by exciting titanium dioxide. When X-rays hit an atom of a material, the oscillating field of the electromagnetic radiation interacts with the electrons bound in the atom. Either the radiation will be scattered by these electrons, or absorbed and excite the electrons. A narrow parallel monochromatic X-ray beam having an initial intensity $I_0$ will, on passing through a sample of thickness "t", be reduced to an intensity I as given by the equation:

$$I = I_0 e^{-(\mu/\rho)\rho t}$$

where $\mu/\rho$ is the mass attenuation coefficient, which depends on the types of atoms and the density $\rho$ of the material.

Figure 1:
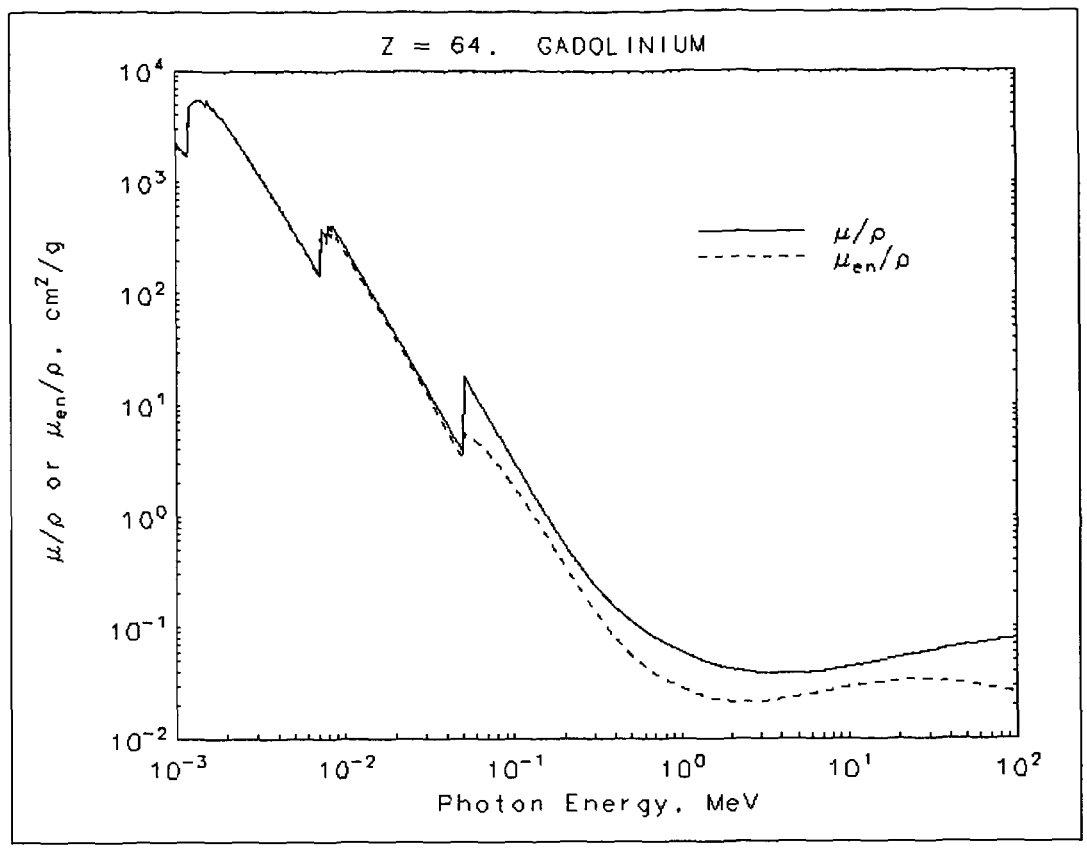
FIG. 1 is a plot of incident photon energy in MeV (shown on the x-axis) against the mass attenuation coefficient (μ/ρ) in $cm^2$/g (shown on the y-axis) for gadolinium (taken from the Physical Reference database, National Institute of Standards and Technology). The graph shows how strongly gadolinium absorbs X-rays at specific incident photon energies.

At certain energies, the absorption of a material increases drastically and gives rise to an absorption edge. Each such edge occurs when the energy of the incident photons is just sufficient to cause excitation of a core electron of the absorbing atom to a continuum state i.e. to produce a photoelectron. The energy of X-ray sources used in apparatus for performing conventional radiotherapy is typically 0.08 to 0.09 MeV. Photoelectrons of X-rays in this energy range are absorbed by rare earth elements and show an absorption edge (see, for example, FIG. 1 for the rare earth element gadolinium). Doping of a metal oxide, such as titanium dioxide, with a material of a high absorption cross-section, such as gadolinium, would, for example, maximize energy absorption.

The invention provides one or more particles, typically a plurality of particles, which each comprise a metal oxide doped with at least one rare earth element, wherein the metal oxide is selected from titanium dioxide ($TiO_2$; also known as titania), zinc oxide (ZnO), cerium oxide ($CeO_2$; also known as ceria) and mixtures of two or more thereof.

Typically, each particle comprises a single metal oxide doped with at least one rare earth element, wherein the metal oxide is selected from titanium dioxide, zinc oxide and cerium oxide.

In one embodiment, the metal oxide is doped with at least two different rare earth elements. Preferably, the metal oxide is doped with at least three different rare earth elements.

Methods for the preparation of doped titanium dioxide particles and doped zinc oxide particles have been described in International patent application numbers PCT/GB99/01685 (WO 99/60994) and PCT/GB00/04587 (WO 01/40114), and in US 2009/0110929. Methods for the preparation of doped cerium oxide particles have been described in International patent application no. PCT/GB02/05013 (WO 03/040270).

Typically, particles of a doped metal oxide are prepared using, for example, standard methods, such as by one of the above methods, and are then subjected to a heating step. It is preferred that a particle of the invention is prepared by heating a particle (i.e. a precursor particle) at a temperature of 400° C. or more, wherein the particle (i.e. precursor particle) comprises a metal oxide which is doped with at least one rare earth element, wherein the metal oxide is selected from titanium dioxide, zinc oxide, cerium oxide and mixtures of two or more thereof. In a preferred aspect, the metal oxide is titanium dioxide. More preferably, the particle is prepared by heating at a temperature of 500° C. or more, particularly 650° C. or more, especially at least 700° C. The particle is heated for at least 2 hours, more preferably at least 3 hours.

In some instances, small amounts of a rare earth element dopant may be present at a surface of the metal oxide, but most of the dopant will be present in the body or host lattice of the metal oxide.

Generally, the host lattice of the metal oxide may be substitution doped or interstitial doped with at least one rare earth element. Preferably, the metal oxide is substitution doped with at least one rare earth element.

It is preferred that the metal oxide is titanium dioxide. The titanium dioxide may be in any form e.g. anatase, rutile or brookite forms. More preferably, the titanium dioxide is in the anatase form. Advantageously, the anatase form of titanium dioxide has a higher intrinsic photoactivity than the other forms of titanium dioxide.

In one embodiment, at least 80% by weight of the titanium dioxide is in the anatase form. It is preferred that at least 85% by weight, particularly at least 90% by weight, of the titanium dioxide is in the anatase form. More preferably at least 95% by weight, especially at least 99% by weight, of the titanium dioxide is in the anatase form.

The reference to "mixtures of two or more" metal oxides in the context of the invention refers to either a mixture of titanium dioxide and zinc oxide; titanium dioxide and cerium oxide; zinc oxide and cerium oxide; or titanium dioxide, zinc oxide and cerium oxide; where at least one of, but preferably each of, the metal oxides is doped with at least one rare earth element.

The term "rare earth element" as used herein refers to an element from the lanthanide group of the Periodic Table, namely La, Ce, Pr, Nd, Pm, Sm, Eu, Gd, Tb, Dy, Ho, Er, Tm, Yb and Lu. All of the isotopes of promethium (Pm) are radioactive. It is therefore preferred that the metal oxide is doped with at least one rare earth element selected from La, Ce, Pr, Nd, Sm, Eu, Gd, Tb, Dy, Ho, Er, Tm, Yb and Lu. The rare earth element is generally present as a dopant in the host lattice of the metal oxide in the form of a cation. When the metal oxide is cerium oxide, then the cerium oxide is preferably doped with at least one rare earth element other than cerium.

The presence of one or more rare earth elements as a dopant in the host lattice of titanium dioxide, zinc oxide or cerium oxide allows these metal oxides to be excited by X-rays to generate free radicals, such as reactive oxygen species (ROS), which have use in the treatment of a human or animal body. The amount of ROS generated by the doped metal oxide will depend on, amongst other things, the identity of the rare earth element dopant and the energy of the X-rays used as part of the treatment. Thus, the metal oxide and the rare earth element(s) should be selected to generate a suitable amount of ROS when X-rays of a specific wavelength (i.e. energy) are used as part of the treatment. This may be achieved by selecting a rare earth element as a dopant that strongly absorbs X-rays at an energy that falls within the energy range of the incident X-rays.

In practice, apparatus that is conventionally used to generate X-rays for medical use, whether for radiotherapy or for diagnostic imaging (e.g. radiography), tends to produce X-rays having energies in certain ranges. Normally, the energy of the X-rays used in radiotherapy tends to be higher than that of those used for diagnostic imaging.

Typically, the metal oxide is doped with at least two different rare earth elements selected from La, Ce, Pr, Nd, Sm, Eu, Gd, Tb, Dy, Ho, Er, Tm, Yb and Lu. More preferably, the metal oxide is doped with at least three different rare earth elements selected from La, Ce, Pr, Nd, Sm, Eu, Gd, Tb, Dy, Ho, Er, Tm, Yb and Lu.

In one embodiment, the metal oxide is doped with gadolinium (Gd). Preferably, the metal oxide is doped with gadolinium and one or more of europium (Eu), erbium (Er) or neodymium (Nd). Thus, the metal oxide may preferably be doped with Gd and Eu; Gd and Er; Gd and Nd; Gd, Eu and Er; Gd, Eu and Nd; Gd, Er and Nd; or Gd, Eu, Er and Nd. More preferably, the metal oxide is doped with gadolinium, europium and erbium.

In another embodiment, the metal oxide is doped with europium. Preferably, the metal oxide is doped with europium and one or more of gadolinium, erbium or neodymium. Thus, the metal oxide may preferably be doped with Eu and Er; Eu and Nd; or Eu, Er and Nd.

In a further embodiment, the metal oxide is doped with erbium. Preferably, the metal oxide is doped with erbium and one or more of gadolinium, europium or neodymium. Thus, the metal oxide may preferably be doped with Er and Eu; or Er and Nd.

In another embodiment, the metal oxide is doped with neodymium. Preferably, the metal oxide is doped with neodymium and one or more of gadolinium, europium or erbium.

In general, the metal oxide is doped with one or more rare earth elements in a total amount of from 0.1 to 25 mol % (e.g. 7.5 to 25 mol %), preferably 1 to 20 mol %, more preferably 2.5 to 15 mol %, especially 5 to 13.5 mol %, and even more preferred is 7.5 to 12.5 mol %.

In one embodiment, the metal oxide is doped with gadolinium and at least one other rare earth metal, wherein the metal oxide is doped with gadolinium in an amount of 1 to 12.5 mol %, preferably from 5 to 10 mol %.

In one embodiment, the metal oxide is doped with (i) gadolinium in an amount of from 3.5 to 12.5% by weight; (ii) europium in an amount of from 0.5 to 1.5% by weight; and (iii) erbium in an amount of from 0.5 to 1.5% by weight. More preferably, the metal oxide is doped with (i) gadolinium in an amount of from 5 to 10% by weight; (ii) europium in an amount of from 0.75 to 1.25% by weight (e.g. about 1% by weight); and (iii) erbium in an amount of from 0.75 to 1.25% by weight (e.g. about 1% weight).

In another embodiment, the metal oxide is doped with (i) gadolinium in an amount of from 3.5 to 12.5 mol %; (ii) europium in an amount of from 0.5 to 1.5 mol %; and (iii) erbium in an amount of from 0.5 to 1.5 mol %. More preferably, the metal oxide is doped with (i) gadolinium in an amount of from 5 to 10 mol %; (ii) europium in an amount of from 0.75 to 1.25 mol % (e.g. about 1 mol %); and (iii) erbium in an amount of from 0.75 to 1.25 mol % (e.g. about 1 mol %).

The total amount of one or more rare earth elements incorporated as a dopant or dopants in the metal oxide will depend on the relative molar amount of the rare earth element containing starting material to the starting material used to prepare the metal oxide. The amount of rare earth element incorporated as a dopant in the metal oxide may depend on the method used to manufacture the particles, which method may be routinely be adapted to obtain the desired amount of dopant in the particles. The amount of rare earth element as a dopant in the metal oxide(s) can readily be measured using techniques that are well known to a person skilled in the art. When a plurality of particles of the invention are present or are used as part of a therapy or treatment, the amounts above in mol % refer to the average (i.e. mean) total amount of the rare earth metal(s) that dope the metal oxide(s) of the particles.

Typically, a particle of the invention has a size of less than 400 nm. This allows the particle to leave the blood stream of a human or animal body. It is preferred that the particle has a size less than 380 nm, especially less than 300 nm. Tumour vasculature is hyperpermeable and has pore sizes from 50 to 600 nm.

Large particles can be sequestered easily by the reticuloendothelial system and may be taken up by the liver or spleen or may be rapidly cleared from the body. It is preferred that a particle of the invention has a size less than or equal to 100 nm. A particle having this size will avoid clearance by phagocytic uptake and hepatic filtration.

Small particles can easily pass through the leaky capillary wall of a tumour. However, the kidneys can also clear very small particles by glomerular filtration. It is preferred that a particle of the invention has a size greater than or equal to 5 nm. A particle having this size will avoid clearance of the particles by the kidneys and to provide good particle retention in a tumour.

Typically, it is preferred that a particle of the invention has a size of from 1 to 100 nm, for example 15 to 50 nm, more preferably 5 to 75 nm (e.g. 10 to 75 nm), particularly 10 nm to 65 nm. The size of the particle may be selected to allow it to enter a cell. For this purpose, the particle preferably has a size less than 65 nm. The particle may also be able to enter an organelle of a cell. To achieve this, it is preferred that the particle has a size less than 50 nm, particularly 20 to 35 nm.

In general, a particle of the invention may have any shape, which may be regular or irregular. The shape of the particles may depend on the method used to prepare them. When the particle is spherical, then the size of the particle simply refers to the diameter of that particle. However, the invention also encompasses particles that are non spherical. In such instances, the size of the particle refers to the diameter of a spherical particle that has the same weight as the particle having a non-spherical shape (i.e. a weight based particle size measurement).

Normally, a distribution of particles having various sizes is obtained. Thus, when there are a plurality of particles of the invention, such as in a pharmaceutical composition, therapy or treatment of the invention, then the sizes described above for a single particle refer to an average (i.e. the mean) size of the particles in a distribution. The average size of the particles in a distribution may be determined using standard centrifuge measurement techniques.

It is to be understood that the invention does not exclude a particle having a core of a biologically inert material, such as silica or alumina, and a layer on the core of the metal oxide doped with at least one rare earth element. However, it is difficult to prepare such particles having a size such as those mentioned above.

It is preferred that a particle of the invention comprises a core consisting of the metal oxide which is doped with at least one rare earth element. Generally, a particle of the invention has a single core consisting of the metal oxide which is doped with at least one rare earth element.

Typically, a particle of the invention has a coating, preferably a coating of one or more compounds selected from silica, alumina, polyethylene glycol, polystyrene, a saccharide, an oligosaccharide, a polysaccharide and mixtures of two or more thereof. The inclusion of a coating on the particles can improve their biocompatibility, prevent them from agglomerating in vivo and allow them to be functionalised with other agents. ROS are generated at a surface of the particle when it comes into contact with water or oxygen. Thus, it is preferred that the coating does not completely cover an outer surface of the metal oxide which is doped with at least one rare earth element. More preferably, the coating is porous.

Any reference to the size of a particle above refers to the total size of the particle, including any coating that may be present. When there is a plurality of particles such that the size is an average particle size, then the size refers to the average total size, including any coating(s) that may be present, of the particles. In general, the thickness of the coating is from 0.1 to 10 nm, preferably from 1 to 5 nm. However, any reference to the size of a particle or particles does not include any linker group, targeting moiety, optical contrast agent, radioisotope, para-magnetic contrast agent, or superparamagnetic contrast agent associated with or attached to the particle.

It is preferred that the coating is silica or sucrose. More preferably, the coating is silica.

Typically, the particles of the invention are for use in the treatment of cancer by administering the particles by injection into a tumour tissue (i.e. intra-tumoral injection) or a cancer site of a subject for treatment. The particles may also be adminstered parenterally.

The particles of the invention may accumulate in a target tissue, such as tumour tissue, by two mechanisms. The first mechanism, so-called passive targetting, is non-specific and relies on the accumulution of the particles in a tumour tissue. This may arise because the tumour has a hyperpermeable vasculature or may have some other physiological abnormality. The second mechanism is a process of active targetting where a targetting moiety (e.g. a ligand) directs the site specific accumulation of the particles at the target tissue. This may be achieved by attaching or conjugating to the particles a targetting moiety that possesses a high affinity for a molecular signature or structure found predominantly or exclusively in the malignant cells. The targeting moiety has a preferential binding affinity for a biological moiety, such as a molecular signature or structure (e.g. a gene, a protein, an organelle, such as mitochondria), which is generally only present in a cancer cell or a tumour tissue. The targeting moiety is capable of concentrating the particles in the tumour tissue or cancer cells.

In an embodiment, a particle of the invention comprises at least one targeting moiety. It is preferred that a targeting moiety is attached to the coating of the or each particle.

Typically, the targeting moiety is a peptide, a polypeptide, a nucleic acid, a nucleotide, a lipid, a metabolite, an antibody, a receptor ligand, a ligand receptor, a hormone, a sugar, an enzyme, a vitamin or the like. For example, the targeting moiety may be selected from a drug (e.g. trastuzumab, gefitinib, PSMA, tamoxifen/toremifen, imatinib, gemtuzumab, rituximab, alemtuzumab, cetximab), a DNA topoisomerase inhibitor, an antimetabolite, a disease cell cycle targeting compound, a gene expression marker, an angiogenesis targeting ligand, a tumour marker, a folate receptor targeting ligand, an apoptotic cell targeting ligand, a hypoxia targeting ligand, a DNA intercalator, a disease receptor targeting ligand, a receptor marker, a peptide (e.g. a signal peptide, a melanocyte stimulating hormone (MSH) peptide), a nucleotide, an antibody (e.g. an antihuman epidermal growth factor receptor 2 (HER2) antibody, a monoclonal antibody C225, a monoclonal antibody CD31, a monoclonal antibody CD40), an antisense molecule, an siRNA, a glutamate pentapeptide, an agent that mimics glucose, amifostine, angiostatin, capecitabine, deoxycytidine, fullerene, herceptin, human serum albumin, lactose, quinazoline, thalidomide, transferrin and trimethyl lysine. Preferably, the targeting moiety is a nuclear localization signal (NLS) peptide. An example of an NLS peptide is PPKKKRKV or CGGFSTSLRARKA. Preferably, the NLS peptide is CGGFSTSLRARKA.

Typically, the targeting moiety is attached to the particle or coating of the particle either covalently or non-covalently. Preferably, a targeting moiety is covalently attached (i.e. by forming a covalent bond) to the coating of each particle.

A targeting moiety can be attached to a particle or a coating of the particle directly or via a linker group. It is preferred that a targeting moiety is attached, particularly covalently attached, to the coating of a particle by a linker group.

The nature of the linker group is not an important part of the invention. However, after administration of the particles to the human or animal body the linker group must remain intact indefinitely or at least for a period of time sufficient to allow active targeting to occur so that there is an accumulation of the particles at the target site of interest. The linker group can be any moiety capable of linking said targeting moiety to the particle or coating of the particle. Such linker moieties are well known in the art.

Typically the linker group has a molecular weight of 50 to 1000, preferably 100 to 500.

In one embodiment, the linker group is a moiety having the formula —OOC(CR$_2$)$_n$COO— where n is an integer from 1 to 10 and each R is independently selected from hydrogen and an optionally substituted C$_1$ to C$_6$ alkyl group. Each optionally substituted C$_1$ to C$_6$ alkyl group may independently be substituted with one or more substituents selected from a halogen atom, hydroxy, $C_1$ to $C_6$ alkoxy, sulfonic acid, sulfonate, phosphoric acid and phosphate. Preferably, each R is hydrogen.

In another embodiment, the linker group is an alkylene moiety having the formula —$(CR'_2)_m$— where m is an integer from 1 to 10 and each R' is independently selected from hydrogen and an optionally substituted $C_1$ to $C_6$ alkyl group, and wherein zero or one to five, preferably one or two, carbon atoms in the alkylene moiety are replaced by a moiety selected from arylene, —O—, —S— and —NR"—, wherein R" is hydrogen or $C_1$ to $C_6$ alkyl and the arylene moiety is unsubstituted or substituted by one, two or three substituents selected from a halogen, hydroxy, $C_1$ to $C_6$ alkyl and $C_1$ to $C_6$ alkoxy group. Each optionally substituted $C_1$ to $C_6$ alkyl group may be independently substituted with one or more substituents selected from halogen atoms, hydroxy, $C_1$ to $C_6$ alkoxy, sulfonic acid, sulfonate, phosphoric acid and phosphate. When at least two carbon atoms of the alkylene moiety are replaced by —O— and/or —NR"—, it is preferred that the carbon atoms which are replaced in the alkylene moiety are not directly adjacent to one another. This avoids the presence of a linker group containing the chemically reactive functional groups —O—O—, —O—NR"— and —NR"—NR"—.

A particle of the invention may further comprise an optical contrast agent, a radioisotope, a paramagnetic contrast agent or a superparamagnetic contrast agent. If one of more of these agents is present, then they may be used to determine whether the particles have accumulated at the target site. Examples of suitable optical contrast agents are Cy5.5 (a combination of chlorotoxin and cyanine); isothiocyanate compounds, such as FITC and TRITC; amine reactive succinimidyl esters, such as NHS-fluorescein; and sulfhydryl reactive maleimide activated fluors, such as fluorescein-5-maleimide. Examples of suitable radioisotopes include copper-67, gallium-66, gallium-67, yttrium-90, yttrium-88, technetium-99m, iodine-123, iodine-125, iodine-131, indium-111, indium-114m and indium-114. An example of a superparamagnetic contrast agent is iron oxide nanoparticle or nanoparticles.

It is preferred that the optical contrast agent, radioisotope, paramagnetic contrast agent or the superparamagnetic contrast agent is attached to the coating of the or each particle. The optical contrast agent, radioisotope, paramagnetic contrast agent, superparamagnetic contrast agent or the targeting moiety may be embedded in, and thereby attached to, the coating during formation of the coating on the particles. This may be achieved simply by mixing the optical contrast agent, radioisotope, paramagnetic contrast agent, superparamagnetic contrast agent or the targeting moiety with the starting materials used to prepare the coating.

Typically, an optical contrast agent, a radioisotope, a paramagnetic contrast agent or a superparamagnetic contrast agent can be attached to a particle or a coating of the particle directly or via a linker group, such as a linker group as described above. The linker group may have a functional group that is able to chelate to a radioisotope. Such a group may be present in the linker compound itself or may be added to the linker once it has been attached to the coating. It is preferred that an optical contrast agent, a radioisotope, a paramagnetic contrast agent or a superparamagnetic contrast agent is attached, particularly covalently attached, to the coating of a particle by a linker group.

The invention also provides a pharmaceutical composition comprising (i) a plurality of the particles of the invention, and optionally (ii) one or more pharmaceutically acceptable ingredients. Suitable pharmaceutically acceptable ingredients are well known to those skilled in the art and include pharmaceutically acceptable carriers (e.g. a saline solution, an isotonic solution), diluents, excipients, adjuvants, fillers, buffers, preservatives, anti-oxidants, lubricants, stabilisers, solubilisers, surfactants (e.g. wetting agents), masking agents, colouring agents, flavouring agents and sweetening agents. Suitable carriers, diluents, excipients, etc. can be found in standard pharmaceutical texts. See, for example, Handbook for Pharmaceutical Additives, 2nd Edition (eds. M. Ash and I. Ash), 2001 (Synapse Information Resources, Inc., Endicott, N.Y., USA), Remington's Pharmaceutical Sciences, 20th edition, pub. Lippincott, Williams & Wilkins, 2000; and Handbook of Pharmaceutical Excipients, 2nd edition, 1994.

A pharmaceutical composition may be in the form (i.e. be formulated as) of a liquid, a solution or a suspension (e.g. an aqueous or a non-aqueous solution), an emulsion (e.g. oil-in-water, water-in-oil), an elixir, a syrup, an electuary, a tablet (e.g. coated tablets), granules, a powder, a lozenge, a pastille, a capsule (e.g. hard and soft gelatine capsules), a pill, an ampoule, a bolus, a tincture, a gel, a paste or an oil.

Typically, the particles of the invention are dissolved in, suspended in, or admixed with one or more pharmaceutically acceptable ingredients.

A pharmaceutical composition suitable for parenteral administration (e.g. by injection) may include an aqueous or non-aqueous, sterile liquid in which the particles of the invention are dissolved or suspended. Such liquids may additionally contain other pharmaceutically acceptable ingredients, such as anti-oxidants, buffers, preservatives, stabilisers, bacteriostats, suspending agents, thickening agents, and solutes that render the formulation isotonic with the blood (or other relevant bodily fluid) of the intended recipient. Examples of excipients include water, alcohols, polyols, glycerol, vegetable oils, and the like. Examples of suitable isotonic solutions for use in such formulations include Sodium Chloride Injection, Ringer's Solution or Lactated Ringer's Injection.

Typically, the concentration of the particles in the pharmaceutical composition is from $1 \times 10^{10}$ particles/ml to $1 \times 10^{24}$ particles/ml, for example from $1 \times 10^{13}$ particles/ml to $1 \times 10^{21}$ particles/ml, more preferably $1 \times 10^{15}$ particles/ml to $1 \times 10^{18}$ particles/ml.

The pharmaceutical composition may be presented in unit-dose or multi-dose sealed containers. Extemporaneous injection solutions and suspensions may be prepared from sterile powders, granules, and tablets.

A pharmaceutical composition suitable for oral administration (e.g by ingestion) includes a liquid, a solution or suspension (e.g. aqueous or non-aqueous), an emulsion (e.g. oil-in-water, water-in-oil), an elixir, a syrup, an electuary, a tablet, granules, a powder, a capsule, a pill, an ampoule or a bolus.

Tablets may be made by conventional means e.g. by compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); preservatives (e.g. methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated, for example, to affect release (e.g. an enteric coating to provide release in parts of the gut other than the stomach).

In general, the pharmaceutical composition will comprise a therapeutically effective amount of the particles of the invention. It will be appreciated by one of skill in the art that appropriate dosages of the particles and a pharmaceutical composition comprising the particles can vary from patient to patient. Determining the optimal dosage will generally involve balancing of the level of therapeutic benefit against any risk or deleterious side effects. The selected dosage level will depend on a variety of factors including the route of administration, the time of administration, the rate of excretion of the particles, the duration of the treatment, other compounds and/or materials used in combination, the severity of the condition, and the species, sex, age, weight, condition, general health, and prior medical history of the patient. The amount of particles and route of administration will ultimately be at the discretion of the physician, veterinarian, or clinician, although generally the dosage will be selected to achieve local concentrations at the site of action that achieve the desired effect.

The invention further provides a combination comprising (a) a plurality of particles of the invention, as described above, and (b) a radiosensitizing agent. Preferably, the radiosensitizing agent is an X-ray radiosensitizing agent. Suitable radiosensitizing agents include misonidazole, metronidazole and tirapazamine. The combination can be used for the treatment of the human or animal body by therapy, be used for the treatment of cancer or be used for the manufacture of a medicament for the treatment of cancer in combination with X-ray radiation, as described herein for the particles or pharmaceutical composition of the invention.

The invention also relates to a pharmaceutical composition as described above, which further comprises (iii) a radiosensitizing agent as described above. It is preferred that the particles of the invention and the radiosensistizing agent form part of a single pharmaceutical composition.

A further aspect of the invention relates to a product comprising (a) a plurality of particles of the invention as described herein, and (b) a radiosensitizing agent as described above, as a combined preparation for simultaneous, concurrent, separate or sequential use in the treatment of cancer when used in combination with X-ray radiation.

The invention also relates to methods and uses for treating, or for the treatment of, cancer, generally when used in combination with X-ray radiation. As part of the therapy or treatment, the particles of the invention, whether as a pharmaceutical composition, combination, product or otherwise, may be administered to a subject by any convenient route of administration. Thus, any reference to the treatment of cancer in combination with X-ray radiation generally refers to the treatment of cancer by administering to a subject a particle or particles of the invention, whether as a pharmaceutical composition, combination, product or otherwise, then directing X-ray radiation to a locus or site of the cancer or tumour tissue.

In general, the cancer treatment of the invention involves administering to a subject a particle or particles of the invention, whether as a pharmaceutical composition, combination, product or otherwise, by injection into a tumour tissue (i.e. intra-tumoral injection) or at a cancer site or locus.

Administration of the particles of the invention is preferably systemic, typically at the site of desired action.

Typically, treating or the treatment of cancer comprises orally (e.g, by ingestion) or, more preferably, parenterally administering to a subject a particle or particles of the invention, whether as a pharmaceutical composition, combination, product or otherwise. It is preferred that parenteral administration is selected from subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid and intrasternal injection.

Generally, a treatment or method for treating cancer of the invention comprises administering a therapeutically effective amount of the particles, whether as a pharmaceutical composition, combination, product or otherwise, to a subject.

Administration can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target tissue or cells being treated, and the subject being treated. Single or multiple administrations can be carried out with the dose level and pattern being selected by the treating physician, veterinarian, or clinician.

In general, a treatment or method for treating cancer of the invention comprises directing a prescribed dosage of X-ray radiation to a locus or site of the cancer or tumour tissue. The X-rays can be administered in one dose, continuously or intermittently (e.g. in divided doses at appropriate intervals) throughout the course of the treatment. Single or multiple doses can be carried out with the dose level and pattern being selected by the treating physician, veterinarian, or clinician.

It is in general unnecessary to use other types of radiation, such as UV radiation, to generate ROS. Thus, it is preferred that a treatment or method for treating cancer of the invention does not involve a step of directing UV radiation to a locus or site of the cancer or tumour tissue. More preferably, the only type of radiation used in a treatment or method for treating cancer of the invention is X-ray radiation.

Typically, a treatment or method for treating cancer of the invention comprises a first step of administering to a subject a particle or particles of the invention, whether as a pharmaceutical composition, combination, product or otherwise, then a second step of directing X-ray radiation to a locus or site of the cancer or tumour tissue, followed by repeating the first and second steps in succession until a prescribed total dose of X-rays has been received by the subject.

Any type of cancer can, in principle, be treated and problems associated with drug resistant tumours are avoided. Thus, the invention may be used to treat a cancer of the lung, liver, kidney, bladder, breast, head and neck, brain, ovaries, prostate, intestine, colon, rectum, uterus, pancreas, eye, bone marrow, lymphatic system or thyroid gland. The invention may be used to treat cancers that are radioresistant, such as renal cell cancer.

Typically, the particles of the invention enhance the effect of radiotherapy in the treatment of a cancer. Thus, the invention relates to the use of the particles, whether as part of a pharmaceutical composition, combination, product, medicament or otherwise, as a radiosensitizing agent, preferably in the treatment of cancer when used in combination with X-rays. A radiosensitizing agent can allow the dosage of X-rays to be reduced without a loss of efficacy, such that a similar therapeutic outcome is obtained compared to that obtained from using higher doses of X-rays in the absence of the particles of the invention. Alternatively, the radiosensitizing agent improves the effect of the X-rays, which results in an improved therapeutic outcome for the patient compared to that obtained when using the same dose of X-rays in the absence of the particles of the invention.

In one embodiment, the treatment or method for treating cancer comprises administering the particles of the invention, whether as a pharmaceutical composition, product, combination or otherwise, to a subject by injection into a tumour tissue or at a cancer site or locus.

Typically, the step of directing X-ray radiation to a locus or site of the cancer or tumour tissue is performed directly after administering the particles to a subject by injection into the tumour tissue or at the cancer site or locus. In some instances, it may be necessary to allow a short period of time for the particles to spread throughout the tumour tissue or cancer site before directing X-ray radiation to the locus. In general, the step of directing X-ray radiation to a locus or site of the cancer or tumour tissue is carried out within 1 hour after administering the particle or the pharmaceutical composition to the subject. Preferably, the step of directing X-ray radiation to a locus or site of the cancer or tumour tissue is carried out within 45 minutes after, more preferably within 30 minutes after, particularly within 15 minutes after, especially within 10 minutes after, even more preferably within 5 minutes, or immediately after administering the particle or the pharmaceutical composition to the subject.

In another embodiment, the treatment or method for treating cancer comprises orally or parenterally administering the particles of the invention, whether as a pharmaceutical composition, product, combination or otherwise, to a subject.

Typically, after administering the particles to a subject, a period of time sufficient to allow the particles to accumulate at the locus of the cancer or tumour tissue is allowed to elapse before directing X-ray radiation to the locus. The time period between administration of the particles and irradiation with X-rays will depend on, amongst other things, the mode of administration, whether there is a targeting moiety attached to the particles and the nature of the cancer.

Typically, the step of directing X-ray radiation to a locus or site of the cancer or tumour tissue is carried out at least 3 hours, especially at least 6 hours, preferably 9 to 48 hours, particularly 12 to 24 hours, after administering, preferably orally or parenterally, the particle or the pharmaceutical composition to the subject.

Generally, the subject is exposed to a total X-ray dose of from 20 to 70 Gy, such as for example 40 to 50 Gy.

Typically, a treatment or method for treating cancer of the invention comprises directing a 1.0 to 3.0 Gy, preferably 1.5 to 2.5 Gy dose, more preferably a 1.8 to 2.0 Gy dose of X-ray radiation to a locus or site of the cancer or tumour tissue. Such small frequent doses are intended to allow healthy cells time to grow to repair any damage caused by the radiation.

Typically, the X-ray radiation in a treatment or method for treating cancer of the invention has an energy from 0.08 MeV to 0.09 MeV.

The method may also comprise a step of detecting the presence or absence of a particle or particles of the invention at a locus or site of the cancer or tumour tissue before directing X-ray radiation to a locus or site of the cancer or tumour tissue. The detecting step may be performed as described below.

The invention provides an in vitro method of destroying cancer cells comprising adding a particle or particles of the invention, whether as a pharmaceutical composition, product, combination or otherwise, to a cell culture, medium or solution comprising cancer cells, then directing X-ray radiation at the cancer cells and particle or particles. Typically, the particle or particles of the invention are left in the presence of the cancer cells in the cell culture, medium or solution for at least 6 hours, preferably at least 12 hours, such as in an incubator, before directing X-ray radiation at the cancer cells and particle or particles.

The invention also relates to a particle or a pharmaceutical composition of the invention for use in a diagnostic method practised on the human or animal body. The invention is concerned with their use for diagnosing the presence or absence of cancer. Also provided is a method for diagnosing the presence or absence of cancer comprising administering to a subject a particle or particles of the invention, whether as a pharmaceutical composition, product, combination or otherwise, then detecting the presence or absence of the particle or particles at a locus or site suspected of being cancerous.

The accumulation of the particles in a target tissue, whether by passive targetting or active targetting, may allow a tumour or cancer to be diagnosed by radiography, typically using conventional X-ray imaging methods. The presence of a heavy rare earth element dopant in the metal oxide of the particles that accumulate in the tumour may allow the tumour tissue to be visualised by X-rays.

Typically, the step of detecting the presence or absence of the particle or particles at a locus or site comprises directing X-rays at the locus or site to obtain an X-ray image. The X-ray image may then be used to determine if a cancer or tumour tissue is present or absent at the locus or site. For diagnostic uses, the exposure time of a subject to X-rays is generally from one second to 30 minutes, preferably from one minute to 20 minutes and more preferably from one second to 5 minutes.

If the particle or particles comprises an optical contrast agent, a radioisotope, a paramagnetic contrast agent or a superparamagnetic contrast agent, then the agent may be used to perform the step detecting the presence or absence of the particle or particles at the locus or site. The exact method of detecting the particle or particles will depend on the optical contrast agent, radioisotope, paramagnetic contrast agent or superparamagnetic contrast agent that is present.

In one embodiment, the presence of a cancer may be diagnosed by detecting an accumulation or abundance of particles of the invention at a locus or site suspected of being cancerous.

Generally, the invention relates to the treatment or diagnosis of mammals, particularly humans.

Definitions

The term "treatment" as used herein in the context of treating cancer refers generally to treatment and therapy, whether of a human or an animal (e.g. in veterinary applications), in which some desired therapeutic effect is achieved, such as, for example, the inhibition of the progress of the condition. The term includes a reduction in the rate of progress, a halt in the rate of progress, regression of the condition, amelioration of the condition, and cure of the condition. Palliative treatment or treatment as a prophylactic measure (i.e. prophylaxis, prevention) are also included.

The term "therapeutically effective amount" as used herein, refers to the amount of a particles of the invention, whether as part of a pharmaceutical composition, product, combination or otherwise, which is effective for producing some desired therapeutic effect when administered in accordance with a desired treatment regimen and when the subject is treated with a prescribed dosage of X-ray radiation.

The term "core" as used herein generally refers to the body of the particle, particularly when the particle does not have a shell or a coating. Typically, the term "core" refers to the central, innermost part of the particle.

The term "shell" as used herein generally refers to a layer, typically an outer layer, that substantially or completely covers an inner surface, such as the surface of the core, of the particle. The term "shell" as used herein is to be understood as referring to a layer made of metallic element or an inorganic compound that absorbs X-rays and emits UV-visible light, such as one or more of $Y_2O_3$, $(Y, Gd)_2O_3$, $CaWO_4$, $GdO_2S$, $LaOBr$, $YTaO_3$, $BaFCl$, $Gd_2O_2S$, $Gd_3Ga_5O_{12}$, $Rb_3Lu(PO_4)_2$, $HfGeO_4$ and $Cs_3Lu(PO_4)_2$, where each compound may optionally be doped with a rare earth element.

Any reference to "composite particle" used herein refers to a particle having a core and at least one shell that is composed of a different material to the core (e.g. a core-shell structure).

Any reference to an "aggregate of particles" used herein refers to a particle, which is an agglomerate of a plurality of smaller, discrete particles, typically nanoparticles. Generally, the aggregate of particles is made up of two different materials, such as a metal oxide and either a metallic element or an inorganic compound that absorbs X-rays and emits UV-visible light (e.g. $Y_2O_3$, $(Y, Gd)_2O_3$, $CaWO_4$, $GdO_2S$, $LaOBr$, $YTaO_3$, $BaFCl$, $Gd_2O_2S$, $Gd_3Ga_5O_{12}$, $Rb_3Lu(PO_4)_2$, $HfGeO_4$ or $Cs_3Lu(PO_4)_2$, where each compound may optionally be doped with a rare earth element).

The term "oligosaccharide" as used herein refers to a saccharide polymer containing a three to ten component monosaccharides. An example of an oligosaccharide is sucrose.

The term "polysaccharide" as used herein refers to a saccharide polymer composed of at least eleven component monosaccharides. An example of a polysaccharide is agarose or dextran.

The term "alkyl" as used herein refers to a monovalent moiety obtained by removing a hydrogen atom from a carbon atom of a hydrocarbon compound typically having from 1 to 6 carbon atoms (unless otherwise specified), which may be aliphatic or alicyclic, and which is saturated. Examples of alkyl groups and moieties include methyl, ethyl, propyl, isopropyl, butyl, isobutyl, tert-butyl, pentyl and hexyl.

The term "halogen atom" as used herein refers to a —F, —Cl, —Br or —I group or moiety.

The term "hydroxyl" as used herein refers to a —OH group or moiety.

The term "alkoxy" as used herein refers to an —O-alkyl group or moiety. Examples of alkoxy groups include —OMe (methoxy), —OEt (ethoxy), —O$^n$Pr (n-propoxy), —O$^i$Pr.

The term "sulfonic acid" as used herein refers to a —S(=O)$_2$OH or —SO$_3$H group or moiety.

The term "sulfonate" as used here refers to a —S(=O)$_2$O$^-$ (e.g. —SO$_3$Na or —SO$_3$K) or —S(=O)$_2$O-alkyl group or moiety. Preferably, sulfonate is a —S(=O)$_2$O$^-$ group or moiety.

The term "phosphoric acid" as used herein refers to a OP(=O)(OH)$_2$ group or moiety.

The term "phosphate" as used herein refers to a —OPO$_3^{2-}$ (e.g. —OPO$_3$Na$_2$) or a —OP(=O)(OH)O$^-$ (e.g. —OP(=O)(OH)ONa) group or moiety. Preferably, phosphate is a —OPO$_3^{2-}$ group or moiety.

The term "alkylene" as used herein refers to a bidentate moiety obtained by removing two hydrogen atoms, either both from the same carbon atom, or one from each of two different carbon atoms, of a hydrocarbon compound having from 1 to 10 carbon atoms (unless otherwise specified), which may be aliphatic or alicyclic, and which is saturated. Examples of alkylene groups include —CH$_2$— (methylene), —CH$_2$CH$_2$— (ethylene), —CH$_2$CH$_2$CH$_2$— (propylene) and —CH$_2$CH$_2$CH$_2$CH$_2$— (butylene).

The term "arylene" as used herein refers to a bidentate moiety obtained by removing two hydrogen atoms, one from each of two different aromatic ring atoms of an aromatic compound, which moiety has from 6 to 10 ring atoms (unless otherwise specified). Preferably, the aromatic compound has 6 ring atoms.

The present invention is further illustrated by the following Examples.

EXAMPLES

Preparation of Rare Earth Doped Titanium Dioxide Particles

One or more rare earth metal compounds selected from gadolinium (III) nitrate hexahydrate, europium (III) nitrate hydrate, terbium (III) nitrate pentahydrate, neodymium nitrate hexahydrate, and erbium (III) nitrate pentahydrate were suspended in 10 mL of titanium(IV) isopropoxide and then 30 mL dry isopropanol was added.

The amount of rare earth metal compound that is suspended in the solution determines the amount of dopant that is introduced into the host lattice of titanium dioxide. A total amount of up to 25 mol % of one or more rare earth elements may be introduced into the host lattice of the titanium dioxide. As an example, 340 micromoles of gadolinium nitrate were added to 34 millimoles of titanium isopropoxide to produce titanium dioxide particles doped with 1 mol % gadolinium.

The solution was then added drop wise to 500 mL of a 50/50 (v/v) water/isopropanol mix whilst stirring vigorously. The mixture was stirred for a further 5 minutes and the precipitate then allowed to settle. The supernatant was removed and the precipitate washed with 200 mL isopropanol and stirred for a further 10 mins. The supernatant was subsequently collected by filtration and then autoclaved in tubes half-filled with ddH$_2$O. The slurry was then kept at 100° C. until dry. Samples were ground to a fine powder and subsequently fired at various temperatures (e.g. 3 hours at 700° C.)

The size distribution of the particles may be analyzed using a CPS Disc Centrifuge®.

The above method may be used to prepare other rare earth doped titanium dioxide particles when alternative rare earth metal nitrate compounds are used. The above method may also be used to prepare rare earth doped cerium oxide or zinc oxide when cerium or zinc ketonates, such as zinc acetylacetonate or cerium acetylacetonate, is used as starting material.

Preparation of Silica Coated Particles

Figure 2:
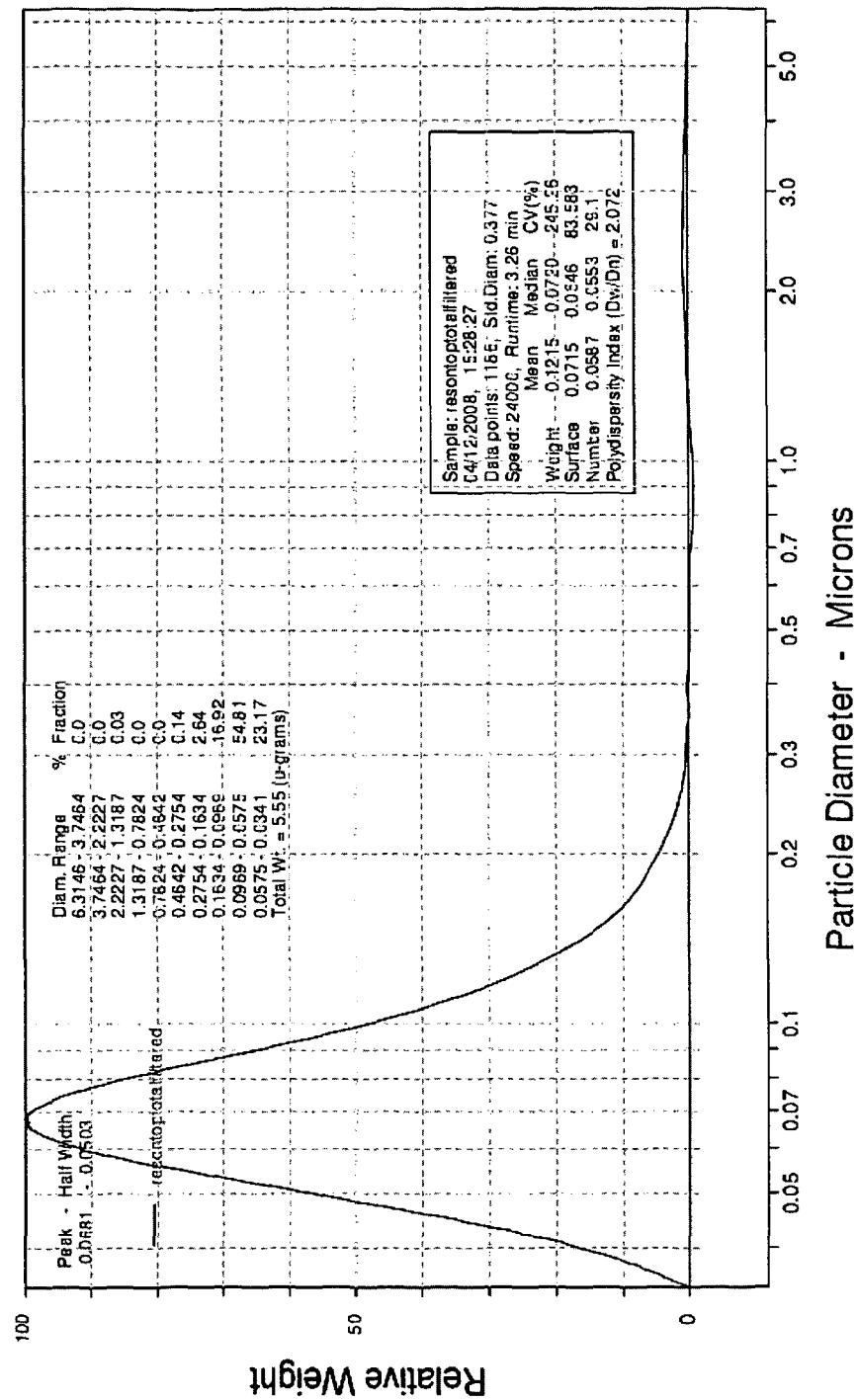
FIG. 2 shows a particle size distribution by weight of titanium dioxide particles doped with gadolinium, in accordance with the invention.

A first solution was prepared by resuspending doped titanium dioxide nanoparticles (4.52 g) in 200 mL Milli-Q water (pH 4.5). A second solution was prepared by adding 3-mercaptopropyltrimethoxy-silane (1.89 mL) to 50 mL Milli-Q water. 20 mL of this second solution was then added to the first solution containing the doped titanium dioxide nanoparticles and was stirred. After 1 hour, sodium silicate (40 mL) was added and samples were removed every 10 mins as the silica layer grows. The samples were then centrifuged and the solids obtained were washed with Milli-Q water. This was repeated three times. The resulting silica coated particles were sonicated in water and passed through a 0.2 micrometer cellulose-acetate filter. The size distribution was analyzed using a CPS Disc Centrifuge®. FIG. 2 shows a particle size distribution of gadolinium doped titanium dioxide prepared by following the method above.

Preparation of FITC Labelled Particles

FITC-APTES was prepared by the addition of 100 μL of 3-aminopropyl triethoxysilane (APTES) to 25 mg of fluorescein isothiocyanate mixed isomers (FITC) in 5 mL of absolute ethanol under a dry nitrogen atmosphere. The mixture was then stirred for 12 hrs. The resulting FITC-APTES (130 μL in 2.25 ml absolute ethanol) was mixed with 130 μL of tetraethylorthosilicate (TEOS), and then 100 μL of ammonium hydroxide (28% in water) was added. The mixture was added to the silica coated particles in 2.5 mL of water and they were sonicated together for 15 mins. The sample was then centrifuged, washed with water and stored in foil.

Estimated ROS Generation from Gadolinium Doped Titanium Dioxide

If an X-ray of 0.085 MeV is used, then the theoretical production of ROS from titanium dioxide particles doped with gadolinium may be calculated. The average energy of the photons in Joules (J) is $1.36 \times 10^{-14}$ J. If a 1 Gy dose (1 Gy=1 J.kg$^{-1}$) of X-rays is administered to a patient, then the average photon flux per kilogram of particles will be:

$$1/1.36 \times 10^{-14} = 7.3 \times 10^{13} \text{ (average) photon flux per kg particles.}$$

The density of gadolinium (III) oxide is 7.41 gcm$^{-3}$ and using an average density of titanium dioxide (the brookite, anatase and rutile forms each have slightly different densities) as 4.00 gcm$^{-3}$, then the mass of a 30 nm particle composed of 90% by mass titanium dioxide and 10% by mass of gadolinium (III) oxide may be calculated as follows:

$$\text{Density } (\rho) \text{ of each particle} = 0.9 \times 4000(TiO_2) + 0.1 \times 7410(Gd_2O_3) = 4341 \text{ kgm}^{-3}.$$

$$\text{Mass of the particle} = 4/3\pi r^3 \rho = 5 \times 10^{-19} \text{ kg}.$$

The number of photons per particle may be calculated as:

$$7.3 \times 10^{13} \text{ photon flux kg}^{-1} \times 5 \times 10^{-19} \text{ kg} = 3.65 \times 10^{-5} \text{ photons.}$$

If a 200 μL sample containing 15 mg ($1.5 \times 10^{-5}$ kg) of particles is administered, then there would be $3 \times 10^{13}$ particles per 200 μL and the average photon flux per 200 μL well would be:

$$3.65 \times 10^{-5} \text{ photons} \times 3 \times 10^{13} \text{ particles} = 1.1 \times 10^9.$$

The total volume of the particles is:

$$1.5 \times 10^{-5} \text{ kg}/4341 \text{ kgm}^{-3} = 3.45 \times 10^{-9} \text{ m}^3.$$

Assuming the particles are present in a well of radius $6 \times 10^{-3}$, then the thickness "t" of particles in the well is:

$$3.45 \times 10^{-9} \text{ m}^3/(\pi \times (6 \times 10^{-3})^2 \text{ m}^2) = 3 \times 10^{-5} \text{ m}.$$

Thus, there is the equivalent of a disc of $3 \times 10^{-5}$ m in height of titanium dioxide doped with gadolinium (TiO$_2$:Gd) in the well. In each well:

$$1.1 \times 10^9 \text{ X-ray photons hit } 3 \times 10^{-5} \text{ m of TiO}_2\text{:Gd.}$$

$$I = I_0 \exp(-0.91 \times 4341 \times 3 \times 10)$$

$$I = 0.88 I_0$$

which means that there are $0.88 \times 1.1 \times 10^9 = 968$ million photons are absorbed per well per 1 Gy of X-ray irradiation.

Assuming that approximately 10% of the absorbed photons result in ROS generation, then 96.8 million ROS are generated per well per 1 Gy of X-ray irradiation.

If each well is seeded with 10000 cells, then there will be 9680 ROS per cell.

Example 1

Figure 3:
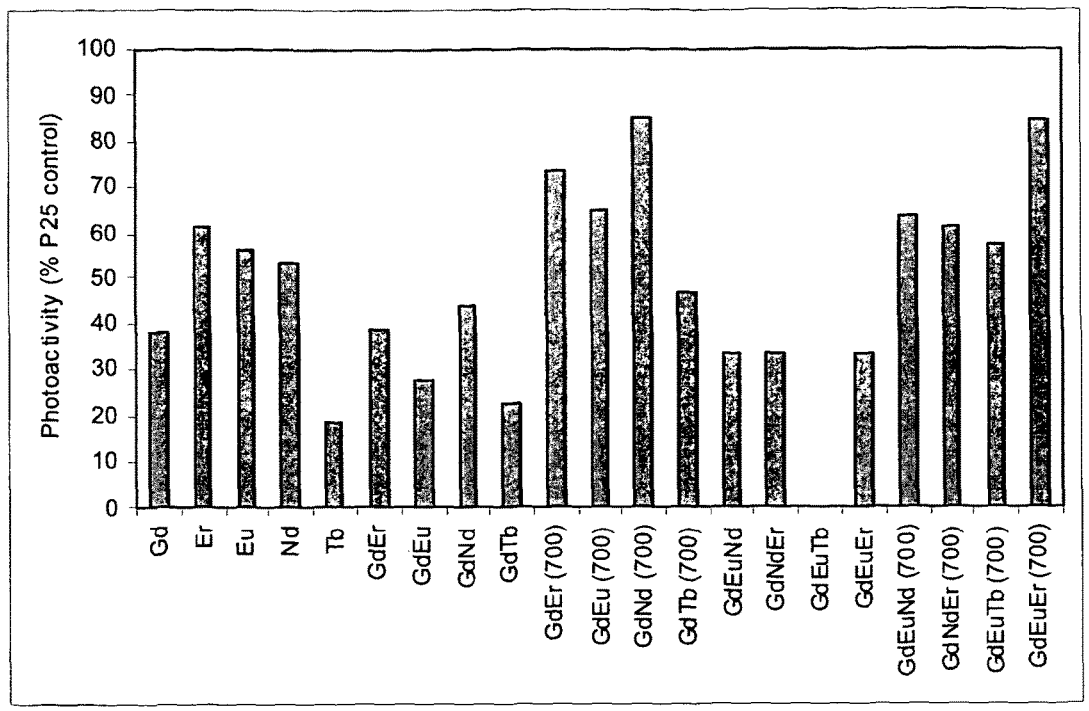
FIG. 3 is a histogram showing the photoactivity of various rare earth elements doped titanium dioxide particles compared to the commercially available titanium dioxide photocatalyst, P25 (Degussa).

Particles of titanium dioxide doped with gadolinium, erbium, europium, neodymium, terbium or combinations of these dopants were prepared according to the method above. The photoactivity of the particles was then tested and measured relative to the commercially available titanium dioxide photocatalyst P25 (Degussa) using a coumarin assay (Ishibashi et al., Electrochemistry Comm., 2 (2000), 207-210). For example, 0.01 g of P25 was added to 8 mL of 2 gL$^{-1}$ of coumarin in PBS. Samples were exposed to either white light from a UVA Cube 400 or a UV lamp. Aliquots were removed at set time intervals (e.g. every 30 mins) and assayed in a fluorimeter (Ex. 345 nm, Em. 496 nm). Activity was expressed as a percent of the activity of P25. The results are shown in FIG. 3.

Figure 4:
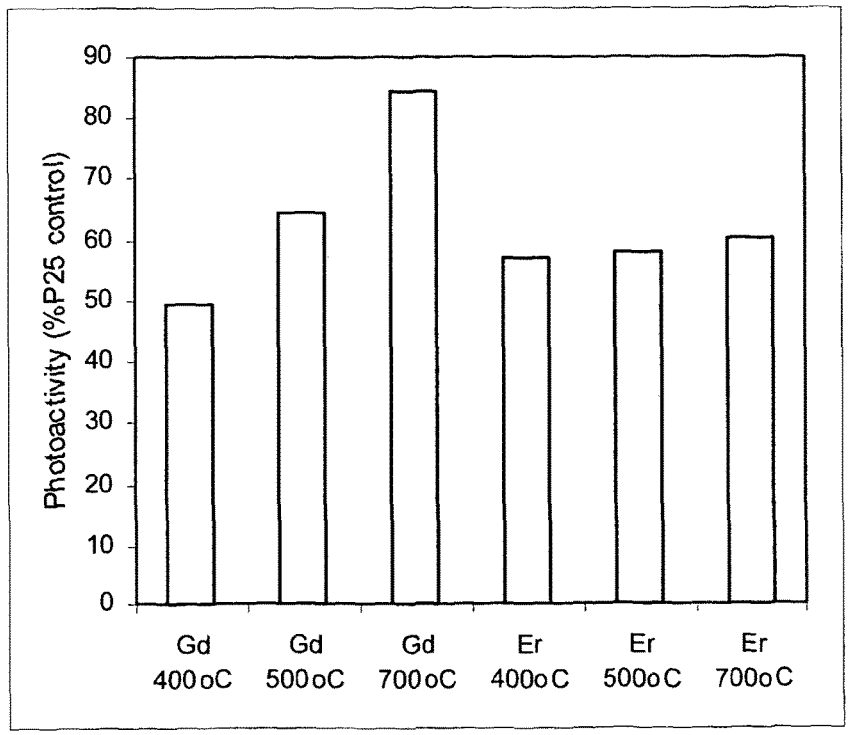
FIG. 4 is a histogram showing the photoactivity of particles of gadolinium doped titanium dioxide and erbium doped titanium dioxide after the particles have been calcined at various temperatures. The photoactivity has been measured relative to the commercially available titanium dioxide photocatalyst, P25 (Degussa).

The particles doped only with gadolinium or erbium were then modified by calcination at various temperatures. The photoactivity of the particles relative to the photocatalyst P25 (Degussa) was again measured. The results are shown in FIG. 4.

These results show that once an electron hole pair is generated within the lattice of the metal oxide, then the metal oxide is photoexcited and de-excited via a significant ROS flux. This proves that the dopant ions do not act as electron hole recombination sites and that ROS will be produced if an X-ray is absorbed.

Example 2

Doped titanium dioxide particles were prepared containing varying concentrations of gadolinium using the above method. The particles were fractionated by size using a 0.2 μm cellulose filter and particles of approximately 65 nm diameter were used for subsequent cell experiments. The silica coated doped titanium dioxide particles are all below 200 nm, with a peak size centred around 65 nm, which should facilitate passive uptake into cells (see FIG. 2). The particles were coated with silica using the method above to prevent aggregation and to promote biocompatibility.

Figure 5:
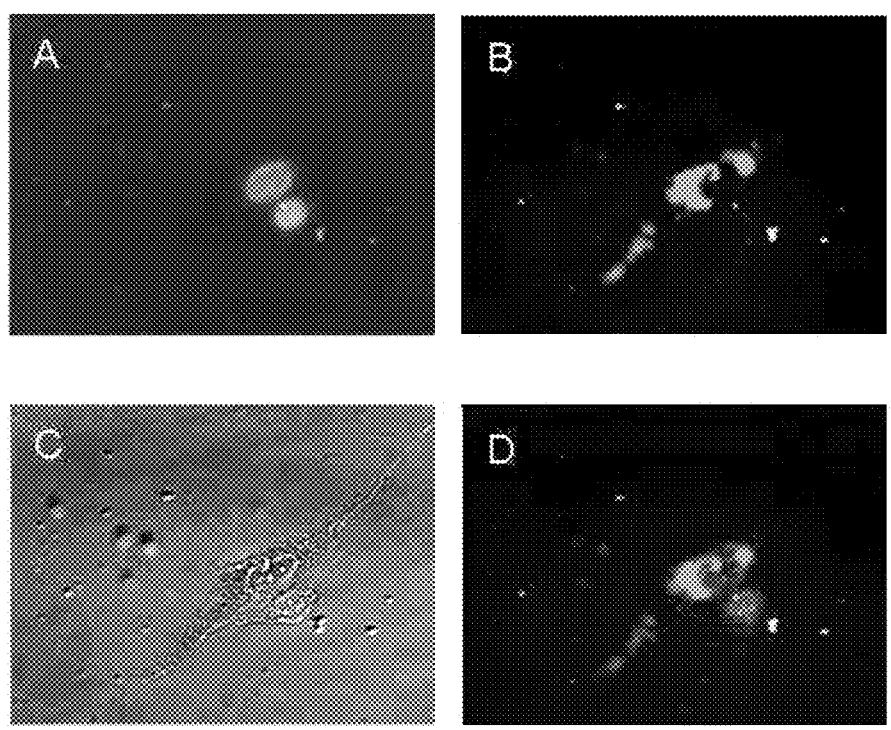
FIG. 5 is a series of slides showing an image of some rhabdosarcoma cells after they were incubated with gadolinium doped titanium dioxide particles. Slide (A) shows the blue fluorescence signal of cells stained with 4',6-diamidino-2-phenylindole (DAPI). Slide (B) shows the green fluorescence signal from the FITC label attached to the silica coating of the gadolinium doped titanium dioxide particles that have entered the cells. Slide (C) is a bright field image of the cells. Slide (D) is a composite image that shows the position of the cell nuclei and the doped titanium dioxide particles.

The silica layer of the particles was labelled with FITC (green). After incubating the cells overnight in the presence of the doped titanium dioxide particles, the particles were found to have passively entered the cells and were localised to endosomes, as shown in FIG. 5. The endosome is in the vicinity of the cell nucleus. The cells show a minimum viability of 80% for all silica coated particles, which demonstrates that they have good bio-compatibility.

An adenoviral nuclear targeting peptide was synthesized with an FITC tag (as described in Tkachenko et al, J. Am.

Chem. Soc., 125 (2003), 4700-4701). The sequence CGGFSTSLRARKA with an N-ter FITC modification and a C-ter amidation was used. The silica coated titanium dioxide particles were incubated with 5% (v/v) APTES and stirred for 1 hour. The particles were then washed with 100 mM Sodium carbonate buffer, pH8.5. A ANB-NOS(N-5-Azido-2-nitrobenzoyloxysuccinimide) cross-linker was then added to the particles in sodium carbonate buffer for 2 hours, followed by the addition of the NLS sequence for 30 minutes. The NLS peptide was then cross-linked to the particles by exposure to UV light at a wavelength of 312 nm.

The FITC-NLS-NP labelled doped titanium dioxide particles were incubated with rhabdosarcoma cells (RH30) overnight at 37° C., 5% $CO_2$. As a control, samples containing cells without doped titanium dioxide were also incubated overnight. Subsequently cells were rinsed with PBS and then fixed with ice-cold methanol. 4',6-diamidino-2-phenylindole (DAPI) was added to stain the cell nuclei. The results are shown in FIG. 5. The position of the cell nuclei is shown by the DAPI fluorescence signal in slide (A) of FIG. 5 (compare it with slide (C), which is a bright field image of the cells). The position of the particles is shown in slide (B), which shows the green fluorescence signal from the FITC label. Slide (D) is a composite image and shows that the particles have entered the cells.

The samples were then irradiated with X-rays at 0.58 Gy $min^{-1}$ to give an exposure of up to 3 Gy. These doses are a conservative representation of a curative treatment that would normally be performed on a patient. For solid epithelial tumours, radiation dose ranges from 50 to 70 Gy would typically be used, whilst lymphomas are generally treated with a dose of 20 to 40 Gy. Such doses would usually be administered as 1.8 to 2 Gy fractions for five days per week. Small frequent doses are intended to allow healthy cells time to grow back after repairing damage due to exposure to radiation.

Following irradiation, the samples were incubated at 37° C. for 24 or 48 hours. After incubation, the cells were washed with phosphate buffered saline (PBS) to remove dead, non-adherent cells. Adherent (live) cells were then trypsinized to permit removal from the multi-well plate. The live cells were then counted using a Neubauer haemocytometer.

Figure 6:
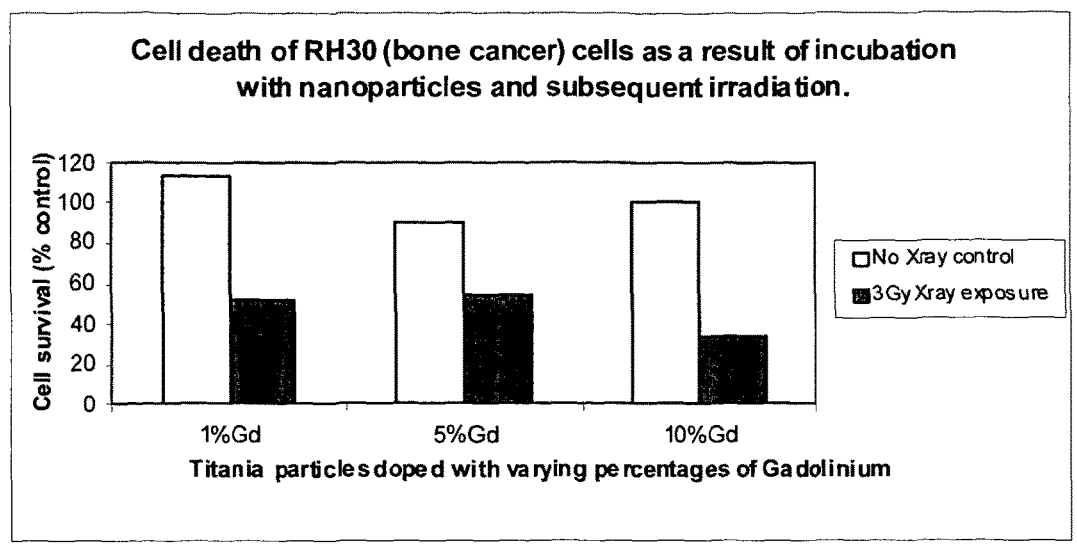
FIG. 6 is a histogram showing the amount of cell death for rhabdosarcoma cells (RH30, a bone cancer derived line) after they have been incubated with titanium dioxide particles doped with varying amounts of gadolinium and then irradiated with X-rays.

Cell viability was expressed as a function of the control samples that without the doped titanium dioxide particles, in order to account for the cell death that resulted solely from exposure to the X-rays. Treatment of the cell lines with the gadolinium doped titanium dioxide particles were found to increase cell death after exposure to X-rays, see the results in FIG. 6. Particles doped with 10% gadolinium can be seen to result in approximately 60% cell death. Virtually no cell death was observed for cell lines that were incubated in the presence of the particles, but which were not excited by X-rays.

Figure 7:
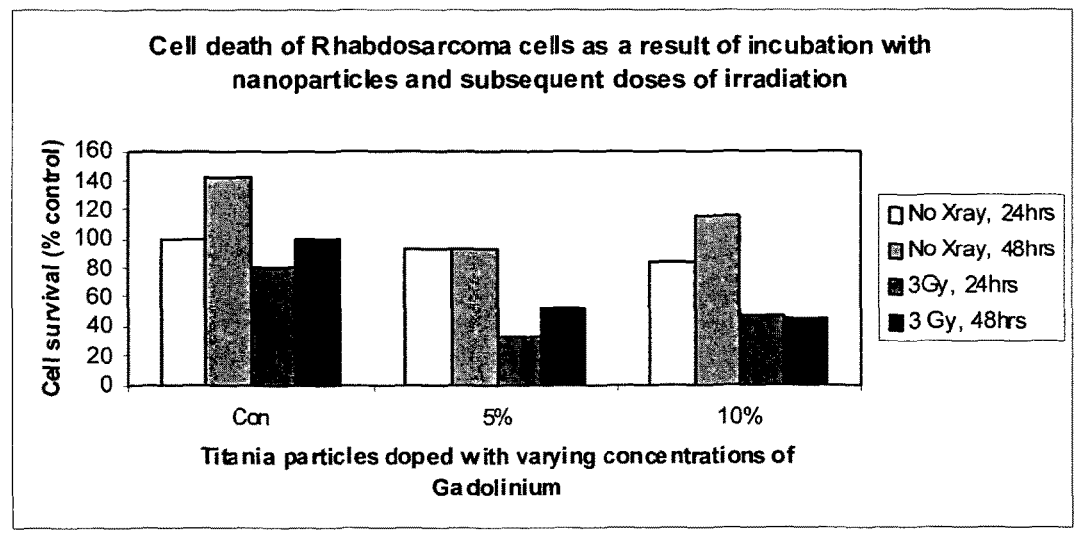
FIG. 7 is histogram showing the amount of cell death for rhabdosarcoma cells that have first been incubated with titanium dioxide particles doped with gadolinium, and then exposed to varying doses of X-rays.

In order to replicate the conditions of a typical cancer treatment, cells were incubated with the particles and were then irradiated with a 3 Gy dose of X-rays. They were then left to recover for 24 hrs and then irradiated again with a further 3 Gy dose of X-rays. Cell death was assessed after 24 hrs and 48 hrs. The results are illustrated in FIG. 7 and show that the treatment not only causes cell death, but also inhibits subsequent cell proliferation. Cell counts showed that cell death was maintained at 60%.

Example 3

Silica coated titanium dioxide particles doped with gadolinium, europium and erbium in varying concentrations were prepared following the methods set out above. Samples containing the RH30 cell line were incubated overnight with the doped titanium dioxide particles, before being irradiated at 0.58 Gy $min^{-1}$ to give an X-ray exposure of 3 Gy. Control samples containing the cell line that was not incubated in the presence of the doped titanium dioxide particles were also irradiated.

Following irradiation, the cells were incubated at 37° C. for 24 or 48 hours, then washed with PBS to remove dead, non-adherent cells. The adherent (live) cells were trypsinized to permit removal from the multi-well plate. Live cells were then counted using a Neubauer haemocytometer.

Figure 8:
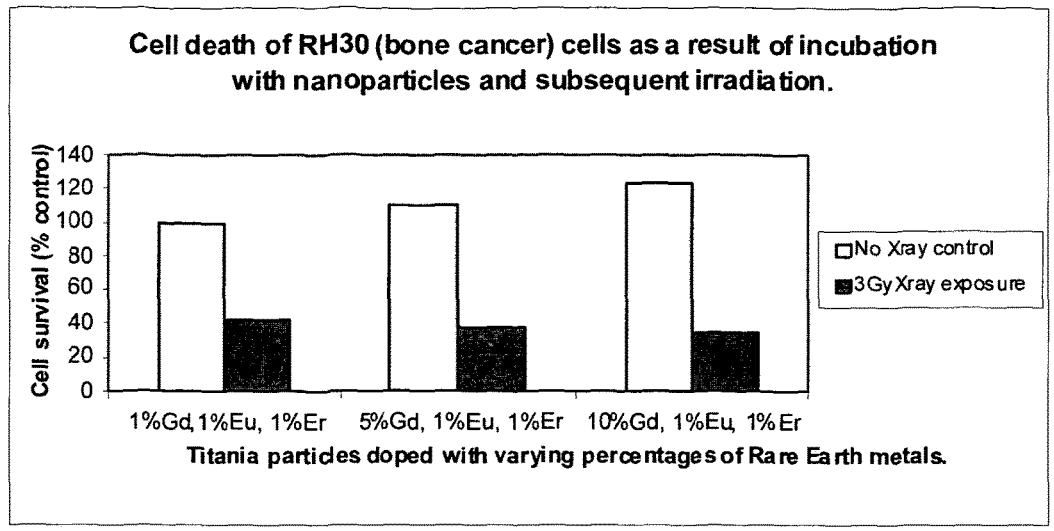
FIG. 8 is a histogram showing the amount of cell death for RH30 (a bone cancer derived line) cells after they have been incubated with titanium dioxide particles doped with varying amounts of gadolinium, erbium and europium and then irradiated with X-rays.

Cell viability was expressed as a function of the control samples that without the doped titanium dioxide particles, in order to account for the cell death that resulted solely from exposure to the X-rays. Cell lines incubated in the presence of titanium dioxide particles doped with varying concentrations of the rare earth elements gadolinium, europium and erbium resulted in approximately 65% cell death (see FIG. 8). Again, there was virtually no cell death for cell lines that were incubated in the presence of the particles, but which were not exposed to X-rays.

Figure 9:
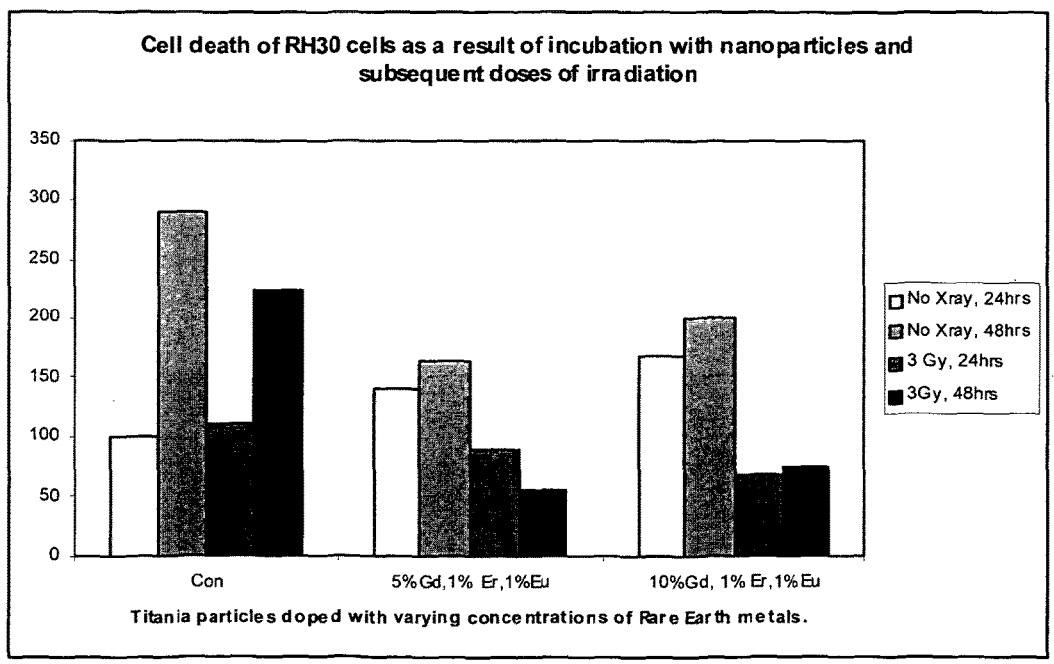
FIG. 9 is histogram showing the amount of cell death for rhabdosarcoma cells that have first been incubated with titanium dioxide particles doped with gadolinium, erbium and europium, and then exposed to varying doses of X-rays.

The conditions of a typical cancer treatment were replicated by irradiating cells that had been incubated with the particles with a 3 Gy dose of X-rays. The cells were then left to recover for 24 hrs and then irradiated again with a further 3 Gy dose of X-rays. Cell death was assessed after 24 hrs and 48 hrs. The results are illustrated in FIG. 9 and show that the treatment not only causes cell death, but also inhibits subsequent cell proliferation. Cell death was again maintained at 60% and the results again support the fact that the treatment also inhibits subsequent cell proliferation.

Further experiments were performed using the titanium dioxide particles doped with gadolinium, erbium and europium with BHK (Hamster kidney derived) and $MCF_7$ (breast cancer derived) cell lines using the method set out in Example 2 above. There was approximately 40% cell death when using these particles.

Example 4

Titanium dioxide particles 30 nm in size (Hombikat XXS100, Sachtleben Chemie, Duisberg) were surface modified with a FITC-NLS peptide and were incubated with A549 cells as described in Example 2 above.

Figure 10:
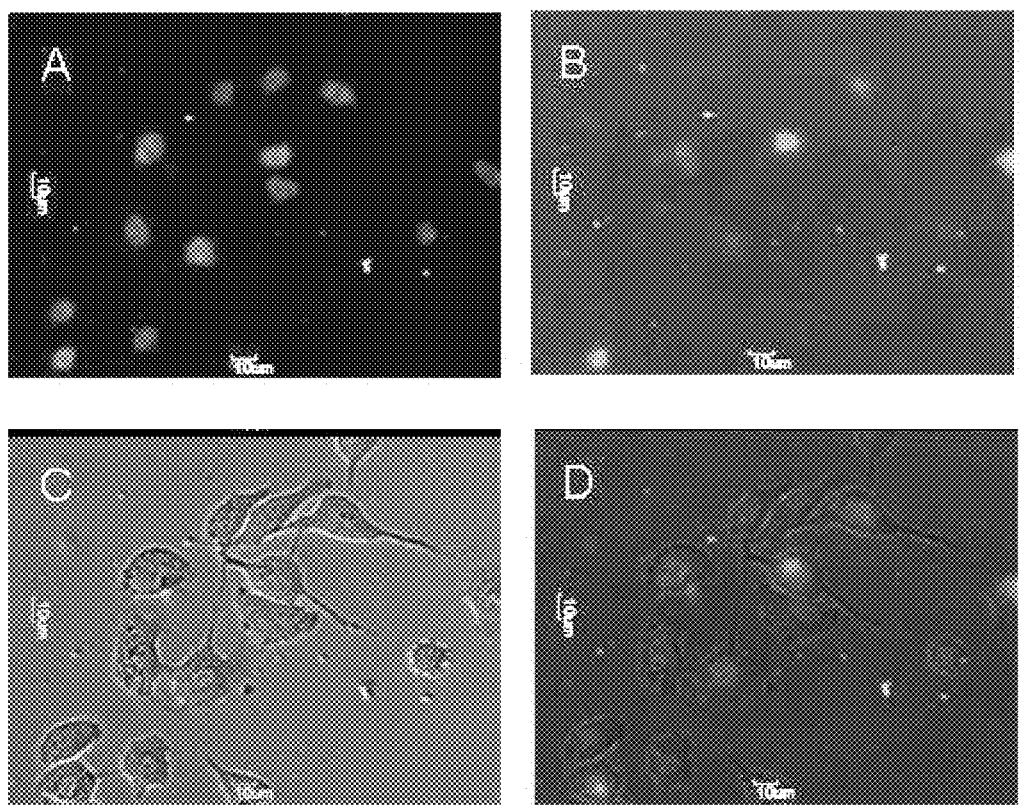
FIG. 10 is a series of slides showing an image of some A549 cells after they were incubated with titanium dioxide particles having a size of 30 nm. Slide (A) shows the blue fluorescence signal of cells stained with 4′,6-diamidino-2-phenylindole (DAPI). Slide (B) shows the green fluorescence signal from the FITC label attached to the silica coating of the gadolinium doped titanium dioxide particles that have entered the cells. Slide (C) is a bright field image of the cells. Slide (D) is a composite image and shows that the particles have localised around the nuclei of the A549 cells.

The results are shown in FIG. 10. The position of the cell nuclei is shown by the DAPI fluorescence signal in slide (A) of FIG. 10 (compare it with slide (C), which is a bright field image of the cells). The position of the particles is shown in slide (B), which shows the green fluorescence signal from the FITC label. Slide (D) is a composite image and shows that the particles have localised around the nuclei of the A549 cells.

Example 5

Tumour cell spheroids were prepared from HepG2 cells by seeding 1% (v/v) agarose wells with 50,000 cells. The cells were incubated at 37° C. under an atmosphere of 5% $CO_2$ until spheroids were formed.

Figure 11:
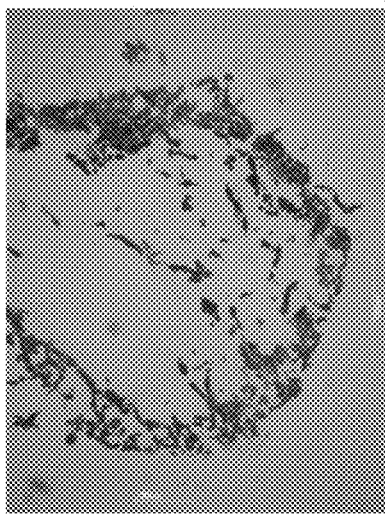
FIG. 11 is a series of slides showing spheroid cells. In A1 the spheroid cells have been incubated with titanium dioxide particles doped with 5 mol % Gd, 1 mol % Eu, 1 mol % Er (A2 is a magnified image of the cells shown in A1), but have not been exposed to X-ray radiation. In B1 the spheroid cell have not been incubated with the titanium particles, but have been irradiated with X-rays (B2 is a magnified image of the cells shown in B1). In C1 the spheroid cells have been incubated with the titanium dioxide particles and have been irradiated with X-rays (C2 is a magnified image of the cells shown in C1).
Figure 11:
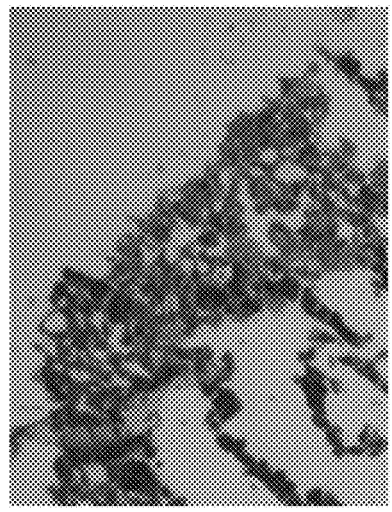
Figure 11:
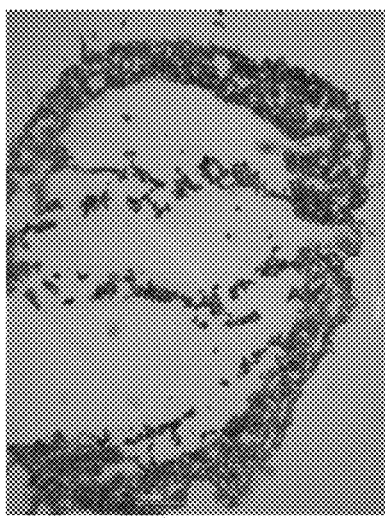
Figure 11:
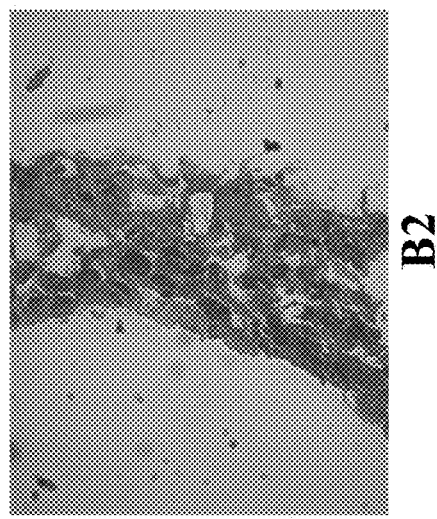
Figure 11:
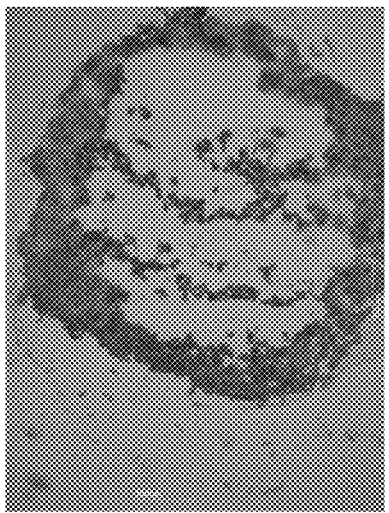
Figure 11:
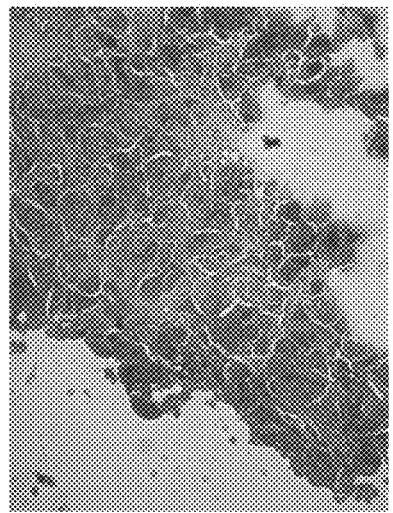

The spheroids were then incubated overnight with titanium dioxide nanoparticles doped with mol % Gd, 1 mol % Eu and 1 mol % Er. Images of the spheroids after incubation are shown in FIG. 11 A1 and A2. The spheroids were then irradiated with X-rays at a dose of 3 Gy and were then returned to the incubator overnight. Images of the spheroids after incubation were then taken and these are shown in FIG. 11 C1 and C2.

As a comparison, spheroids that were not incubated with titanium dioxide nanoparticles were also irradiated with X-rays at a dose of 3 Gy. After irradiating the spheroids and incubating them overnight, the images shown in FIG. 11 B1 and B2 were obtained.

It is clear from comparing C1 and C2 with B1, B2, A1 and A2 in FIG. 11 that incubating the spheroids with the titanium dioxide nanoparticles and then irradiating them with X-rays caused a greater loss of contiguity of the spheroid cells compared to just incubating them with the nanoparticles (as shown in A1 and A2) or irradiating them with X-rays (as shown in B1 and B2). The contiguity of the spheroid cells was not affected when they were incubated with the nanoparticles without being irradiated with X-rays.

The invention claimed is:

1. A method of treating cancer in a subject comprising:
    administering a particle to a locus or site of the cancer or to tumour tissue in the subject, which particle comprises a metal oxide, which metal oxide is titanium dioxide doped with from 0.1 to 25 mol % of at least one rare earth element, wherein the titanium dioxide is a host lattice and the at least one rare earth element is present as a dopant within said host lattice; and
    applying X-ray radiation suitable for radiotherapy to the locus or site of the cancer or tumour tissue and thereby exciting the metal oxide in the particle at the locus or site of the cancer or tumour tissue and generating reactive oxygen species at the locus or site of the cancer or tumour tissue.

2. The method according to claim 1, wherein the particle comprises a core consisting of titanium dioxide doped with from 0.1 to 25 mol % of at least one rare earth element.

3. The method according to claim 1, wherein the metal oxide is doped with at least two different rare earth elements.

4. The method according to claim 1, wherein the metal oxide is doped with gadolinium.

5. The method according to claim 1 wherein the metal oxide is doped with europium.

6. The method according to claim 1 wherein the metal oxide is doped with erbium.

7. The method according to claim 1 wherein the metal oxide is doped with neodymium.

8. The method according to claim 1, wherein the particle has a size of less than 400 nm.

9. The method according to claim 1, wherein the particle has a coating comprising silica, alumina, polyethylene glycol, polystyrene, a saccharide, an oligosaccharide, a polysaccharide or a mixture of two or more thereof.

10. The method according to claim 9 wherein a targeting moiety is attached to the coating.

11. The method according to claim 9, wherein an optical contrast agent, a radioisotope, a paramagnetic contrast agent or a superparamagnetic contrast agent is attached to the coating.

12. The method according to claim 1 wherein the cancer is a cancer of the lung, liver, kidney, bladder, breast, head, neck, brain, ovaries, prostate, intestine, colon, rectum, uterus, pancreas, eye, bone marrow, lymphatic system or thyroid gland.

13. The method according to claim 1 comprising:
    (a) administering the particle by intra-tumoral injection into the tumour tissue or at the cancer site or locus; or
    (b) parenterally administering to the subject the particle and allowing the particle to localize at the locus or site of the cancer or tumour tissue.

14. The method according to claim 1 further comprising the step of detecting the presence of the particle at the locus or site of the cancer or tumour tissue before directing X-ray radiation to the locus or site of the cancer or tumour tissue.

15. An in vitro method of destroying cancer cells comprising adding a particle to a cell culture, medium or solution comprising cancer cells, then directing X-ray radiation at the cancer cells, wherein the particle comprises a metal oxide, which metal oxide is titanium dioxide and is doped with from 0.1 to 25 mol % of at least one rare earth element, and wherein the titanium dioxide is a host lattice and the at least one rare earth element is present as a dopant within said host lattice.

16. A method according to claim 1, wherein the host lattice is substitution doped or interstitial doped with the at least one rare earth element.

17. A method according to claim 1, wherein the host lattice is substitution doped with the at least one rare earth element.

* * * * *